United States Patent [19]
Barbera-Guillem

[11] Patent Number: 6,074,643
[45] Date of Patent: Jun. 13, 2000

[54] SITE-DIRECTED CHEMOTHERAPY OF METASTASES

[75] Inventor: Emilio Barbera-Guillem, Columbus, Ohio

[73] Assignee: CLI Oncology, Inc., Jamestown, N.Y.

[21] Appl. No.: 08/882,447

[22] Filed: Jun. 26, 1997

Related U.S. Application Data

[60] Continuation-in-part of application No. 08/680,372, Jul. 15, 1996, abandoned, which is a division of application No. 08/118,969, Sep. 9, 1993, Pat. No. 5,536,642.

[51] Int. Cl.$^7$ .................................................. A61K 39/395
[52] U.S. Cl. .................. 424/178.1; 424/1.49; 424/182.1; 424/183.1; 514/23; 436/827
[58] Field of Search ................. 424/1.49, 178.1, 424/182.1, 183.1; 514/23; 436/827

[56] References Cited

U.S. PATENT DOCUMENTS 5,639,737  6/1997  Rubin ......................................... 514/53

OTHER PUBLICATIONS

Lazzaro, et al., Experimental Hematology, vol. 23, pp. 1347–1352, 1995.

*Primary Examiner*—Sheela Huff
*Attorney, Agent, or Firm*—M. Bud Nelson

[57] ABSTRACT

Provided for use in site-directed chemotherapy are compositions comprising chemotherapeutic agents targeted to either arrested metastatic cells via a cell-surface marker associated with metastasis; or are targeted to type 1 endothelial cells of the tissue comprising the organ site at which metastatic cells arrest such that (a) any arrested metastatic tumor cells are then exposed to the chemotherapeutic agent, and/or (b) the endothelial cells are altered thereby inhibiting the ability of the metastatic tumor cells to arrest, survive or proliferate in that site. Also provided are methods of site-directed chemotherapy of metastatic cells of non-lymphoid tumor origin. Site-directed chemotherapy comprises introducing a therapeutically effective amount of a chemotherapeutic agent directly into a vascular access of the organ having, or suspected of having, arrested metastatic cells thereby concentrating the therapy in the prometastatic territories of the treated organ.

12 Claims, 12 Drawing Sheets

LEC-1 +TNFα

LEC-2 +TNFα

Prometastatic Territory

Non Prometastatic Territory

Drug free, Cancer cell Free

Unwanted damage

Normal cell with marker

Desired effect

Tumor cell with marker

Failure

Tumor cell without marker

SITE-DIRECTED CHEMOTHERAPY OF METASTASES

This application is a continuation-in-part of my earlier application U.S. Ser. No. 08/680,372, filed Jul. 15, 1996, now abandoned, which is a divisional of earlier application U.S. Ser. No. 08/118,969, filed on Sep. 9, 1993, now U.S. Pat. No. 5,536,642, each application is herein incorporated by reference.

FIELD OF THE INVENTION

The present invention relates to a novel discovery, and characterization, of the nature of the site in particular organs/tissues for which metastatic tumor cells exhibit a biological predilection and specificity in arresting and surviving for subsequent development. More particularly, the present invention relates to methods for directing chemotherapy to the site in particular organs where metastases arrest and develop.

BACKGROUND OF THE INVENTION

1. Metastasis.

Metastasis is the spread of malignant tumors to secondary sites remote from the original or primary tumor. Metastasis presents a cancer clinician with difficulty in diagnosing and treating the malignant tumor because (a) metastases may be comprised of as little as one or a few cells thereby evading clinical diagnosis even with modern techniques; (b) often metastases have already been seeded by the time a patient is diagnosed with a malignant non-lymphoid tumor (Silverberg et al., 1989, CA Cancer J. Clin. 39:3–21); (c) treatment is more complex than simple surgical excision of the primary tumor; (d) systemic therapy for metastatic non-lymphoid tumors, such as renal cell carcinoma (Rosenberg et al., 1985, N. Engl. J. Med. 313:1485–1492), remains ineffective with little survival advantage; and (e) not all malignant tumors have the same metastatic potential, and no tumor-specific serum marker has been described for determining whether any particular non-lymphoid tumor will develop metastasis.

While new therapeutics are being developed and tested for efficacy, many of the currently available cancer treatments are relatively ineffective. It has been reported that chemotherapy results in a durable response in only 4% of treated patients, and substantially prolongs the life of only an additional 3% of patients with advanced cancer (Smith et al., 1993, J. Natl. Cancer Inst. 85:1460–1474). Current treatments for metastases are both cost-prohibitive, relatively ineffective, and present with major toxicity. Regarding the latter and depending on the drug or drug combination used, systemic chemotherapy may result in one or more toxicities including hematologic, vascular, neural, gastrointestinal, renal, pulmonary, otologic, and lethal.

Regarding cost and efficacy, women with limited metastatic breast cancer may benefit (by adding approximately 27 months to the average woman's life) from high dose chemotherapy with autologous bone marrow transplantation at a cost that may range from at least $100,000 to $250,000 per person, as compared to the cost of treating early stage breast cancer that may range from about $10,000 to $15,000 (Smith et al., 1993, supra) . As another example, of the more than 150,000 Americans who will develop colorectal carcinoma each year, it is estimated that 17% to 55% of them will develop or already have metastases in the liver (Zaveidsky et al., 1994, Am. Surgeon 60:929–933). Surgery, when possible, is used as a standard therapy for patients with isolated metastases (e.g., hepatic and/or pulmonary). After resection, the projected five year survival rate may range from 25–35%, the mean survival is about 31 months, and the 30-day mortality rate is about 4% (Wade, 1996, J. Am. Coll. Surg. 182:353–361). However, about 25% to 45% of patients who have had resection of their colorectal cancer later develop recurrences (Zaveidsky et al., 1994, supra). As yet another illustration, some 40% of the patients with prostate cancer present with disseminated disease at the time of diagnosis, and up to 80% of that total will develop bone metastases (Alcover et al., 1994 Actas. Urol. Esp. 18(S):409–416). The ten year survival rates for prostate cancer patients are 75% when the cancer is confined to the prostate, 55% with regional extension, and 15% with distant metastases (Potosky et al., 1995, JAMA 273:548–552).

Thus, the background and related art fail to disclose methods for administering anticancer therapy against metastatic cells form non-lymphoid tumors directly to the areas in organs where metastases develop ("prometastatic territories"), rather than conventional systemic administration. Hence, a need still exists for a relatively cost-effective and efficient method for treating metastatic cells in the organ site in which they arrest and may subsequently develop into metastatic foci. Such a method would be an approach to ameliorate toxicity associated with systemic chemotherapy, as well as to concentrate the chemotherapeutic agent(s) in the proximity of the metastatic cells.

SUMMARY OF THE INVENTION

Accordingly, it is a primary object of the present invention to provide chemotherapeutic agents which can be used in a site-directed method for chemotherapy of metastases.

It is another object of the present invention to provide a method for chemotherapy directed to metastases which are localized in particular organs.

It is a further object of the present invention to provide a method for site-directed chemotherapy of metastases that may be a cost-effective alternative to the relatively high cost of systemic chemotherapy of metastases.

It is also a further object of the present invention to provide a method for site-directed chemotherapy of metastases which may ameliorate toxicity associated with systemic chemotherapy, as well as to better concentrate the chemotherapeutic agent(s) in the proximity of the metastatic cells.

The foregoing objects are achieved by providing novel compositions which are targeted to the sites at which metastatic cells arrest in organs in which metastases develop. The compositions are targeted to either the arrested metastatic cells themselves via a cell-surface marker associated with metastasis; or are targeted to specific endothelial cells of the tissue comprising the organ site at which metastatic cells arrest such that (a) any arrested metastatic tumor cells are then exposed to the chemotherapeutic agent, and/or (b) the endothelial cells are altered thereby inhibiting the ability of the metastatic tumor cells to arrest, survive, or proliferate in that site. These and further features and advantages of the invention will be better understood from the description of the preferred embodiments when considered in relation to the figures in which:

DETAILED DESCRIPTION OF THE PREFERRED EMBODIMENTS

Definitions

Figure 1:
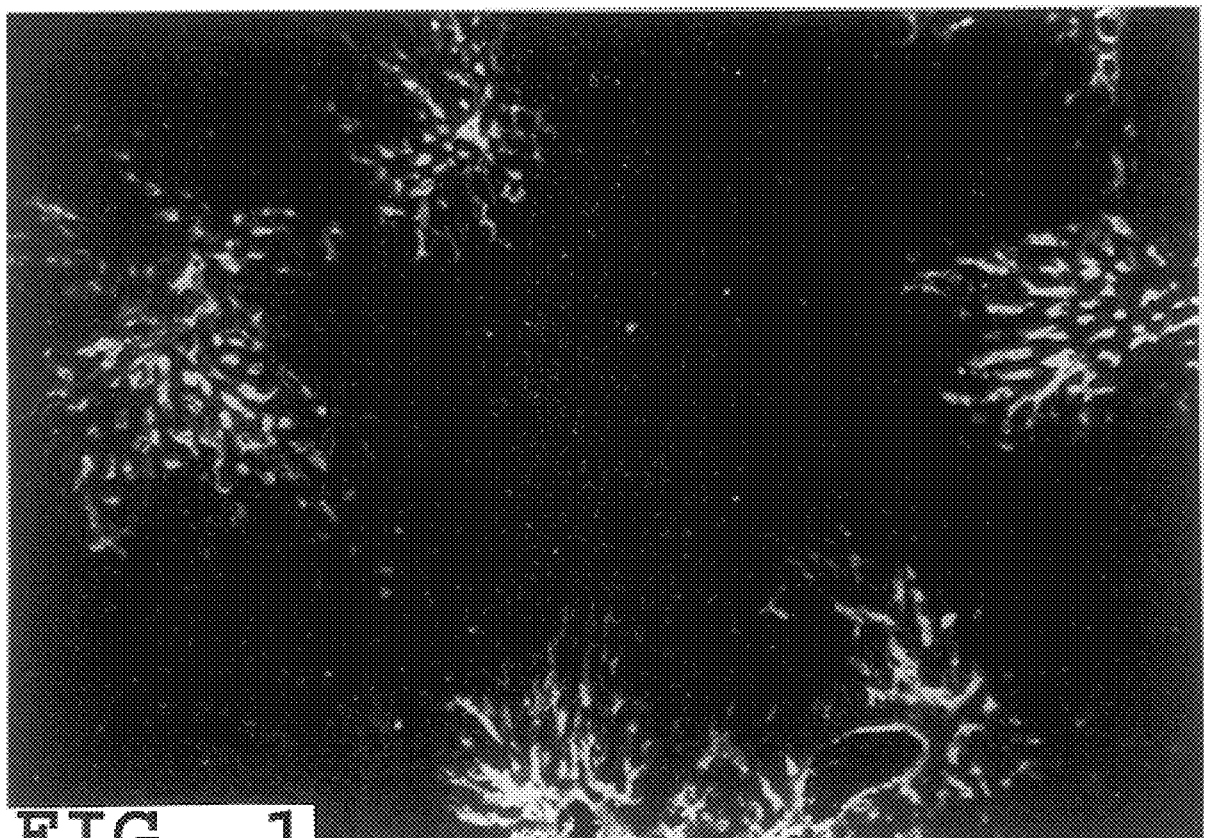
FIG. 1 is a photograph of a liver section showing the binding specificity of wheat germ agglutinin, tagged with rhodamine, for type 1 endothelial cells in the prometastatic territories (bright zones) versus cells within the rest of the liver structure (dark areas).

The term "antibody fragment" or "fragment thereof" is used herein, for purposes of the specification and claims, to mean a portion or fragment of an intact antibody molecule, wherein the fragment retains antigen-binding function; i.e., F(ab')$_2$, Fab', Fab, Fv, Fd' and Fd fragments. Methods for producing the various fragments from MAbs are well known to those skilled in the art.

The term "conjugate" or "chemotherapeutic agent" is used herein, for purposes of the specification and claims, to mean a composition comprised of at least one targeting molecule according to the present invention, and at least one antitumor agent. Such antitumor agents are known in the art and include, but are not limited to, toxins, drugs, enzymes, cytokines, radionuclides, photodynamic agents, and angiogenesis inhibitors. Toxins include ricin A chain, mutant Pseudomonas exotoxins, diphtheria toxoid, streptonigrin, boamycin, saporin, gelonin, and pokeweed antiviral protein. Drugs include cytotoxic drugs including, but not limited to, 5-fluorouracil (5-FU), daunorubicin, cisplatinum, bleomycin, melphalan, taxol, tamoxifen, mitomycin-C, and methotrexate. Radionuclides include radiometals. Photodynamic agents include porphyrins and their derivatives. Angiogenesis inhibitors are known in the art and include natural and synthetic biomolecules such as paclitaxel, O-(chloroacetyl-carbomyl) fumagillol ("TNP-470" or "AGM 1470"), thrombospondin-1, thrombospondin-2, angiostatin, human chondrocyte-derived inhibitor of angiogenesis ("hCHIAMP"), cartilage-derived angiogenic inhibitor, platelet factor-4, gro-beta, human interferon-inducible protein 10 ("IP10"), interleukin 12, Ro 318220, tricyclodecan-9-yl xanthate ("D609"), irsogladine, 8,9-dihydroxy-7-methyl-benzo[b]quinolizinium bromide ("GPA 1734"), medroxyprogesterone, a combination of heparin and cortisone, glucosidase inhibitors, genistein, thalidomide, diamino-antraquinone, herbimycin, ursolic acid, and oleanolic acid. Also, the chemotherapeutic agent may further comprise a pharmaceutically acceptable carrier medium for facilitating infusion into the vascular access of the patient's organ to be treated. Such pharmaceutically acceptable carrier media are known to those skilled in the art to include buffered saline solutions, buffered carbohydrate solutions, liposomes (Phillips et al., 1994, *J. Immunother. Emphasis Tumor Immunol.* 15:185–93), and the like. The methods for complexing the targeting molecule(s) with at least one antitumor agent are well known to those skilled in the art (See, for example, antibody conjugates as reviewed by Ghetie et al., 1994, *Pharmacol. Ther.* 63:209–34). Often such methods utilize one of several available heterobifunctional reagents used for coupling or linking molecules.

The term "metastases" or "metastatic tumor cell" is used herein, for purposes of the specification and claims, to mean a metastasis from a primary tumor wherein the primary tumor is a solid, non-lymphoid tumor, as will be more apparent from the following embodiments.

The term "monoclonal antibody" is used herein, for purposes of the specification and claims, to mean murine monoclonal antibodies, and engineered antibody molecules such as chimeric or "humanized" antibodies (as reviewed by Adair, 1992, *Immunol. Reviews* 130:6–37, herein incorporated by reference).

The term "organ in which metastases develop" is used herein, for purposes of the specification and claims, to mean any tissues or organs in which metastases of solid, non-lymphoid tumors develop including liver, lung, brain, lymph node, bone marrow, and adrenal gland.

The term "targeting molecule" is used herein, for purposes of the specification and claims, to mean at least one composition selected from the group consisting of a lectin having binding specificity for N-acetyl neuraminic acid (NANA) and/or N-acetyl galactosamine (GalNAC), a carbohydrate compound or composition comprising mannose, a compound or composition comprising glycated albumin, a monoclonal antibody or fragment thereof having binding specificity for an endothelial cell adhesion molecule that is preferentially expressed by type 1 endothelial cells as compared to other subpopulations of endothelial cells contained in the sinusoidal area of an organ in which metastases develop (e.g., intracellular adhesion molecule-1 (ICAM-1)), a monoclonal antibody or fragment thereof having binding specificity for IL-2Rα, and a composition comprising IL-2. In that regard, lectins having such specificity are known to those skilled in the art, and include but are not limited to lectins binding GalNAC such as Dolichos biflorus agglutinin (DBA), soybean agglutinin (SPA), Maclura pomifera agglutinin (MPA), Phaeolepiota aurea lectins 1 and 2 (PAL-I, PAL-II), Moluccella laevis lectin (MLL), peanut agglutinin (PNA), Vicia villosa agglutinin (WA), Sophora japonica agglutinin (SJA), Caragana arborescens agglutinin (CAA), Griffonia simplicifolia lectin (BSI-A4), Bauhinia purpurea agglutinin (BPA), and Helix aspersa agglutinin (HAA); lectins binding NANA such as Limax flavus lectin (LFA), and limulin; and lectins binding both GalNAC and NANA including wheat germ agglutinin (WGA).

The terms "preferentially expressed by type 1 endothelial cells" is used herein, for purposes of the specification and claims, to mean a molecule expressed on the surface of type 1 endothelial cells, wherein the level of expression (measured directly or indirectly, and including by presence or by activity) of such molecule is at least 3 to 4 times that expressed by other subpopulations of endothelial cells contained in the sinusoidal area of an organ in which metastases develop. Thus, preferential expression may include detection of expression of the molecule on or by type 1 endothelial cells, and absence of detection of the same molecule on or by type 2 endothelial cells; or a log greater expression of the same molecule on or by type 1 endothelial cells as compared to expression on or by type 2 endothelial cells.

A drawback to systemic chemotherapy is the lack of selectively delivering the therapy to its intended target, diseased tissue, rather than to normal tissue. Because of the lack of such "site-directed" chemotherapy, toxicity of normal tissue is often a side effect associated with systemic chemotherapy. The present invention relates to compositions, and a method for delivering the compositions, which are targeted to the sites at which metastatic cells arrest in organs in which metastases develop.

Metastasis is a process determined by the nature of the tumor cells (the "seed") as well as by the nature of the site (the "soil") at which metastases arrest and survive for potentially and subsequently developing into metastatic foci. The nature of the metastasizing tumor cell, such as markers which are associated with and expressed by the metastasizing tumor cell, and the site at which the metastasizing tumor cells arrest and survive each represent a target in the metastatic process for therapeutic intervention by chemotherapy. It will be apparent from the present invention that metastatic tumor cells exhibit a biological predilection and specificity for arresting and surviving in certain areas of organs in which metastases develop. Thus, the compositions of the present invention, and the method for delivering such compositions, are targeted to either the arrested metastatic cells themselves via a cell-surface marker associated with metastasis; or are targeted to specific endothelial cells of the tissue comprising the organ site at which metastatic cells arrest such that (a) any arrested metastatic tumor cells present are then exposed to the chemotherapeutic agent, and/or (b) the endothelial cells are altered thereby inhibiting the ability of metastatic tumor cells present to arrest, survive, or proliferate in that site.

The present invention relates to identification of two tumor markers which are associated with metastasis. Disclosed by inventor Dr. Barberá in U.S. Pat. No. 5,536,642, is the tumor cell marker IL-2Rα which is highly sensitive and specific for metastasis of primary solid, nonlymphoid tumors, and which may be used in diagnostic or prognostic assays in guiding treatment regimens, and further represents a target for methods of anticancer therapy directed against tumors expressing IL-2Rα. Also disclosed in U.S. Pat. No. 5,536,642, is the joint invention relating to the tumor cell marker TCRβ as marker of metastasis useful in diagnostic or prognostic assays in guiding treatment regimens (embodiments disclosing the same are included herein as well), and represents a target for methods of anticancer therapy directed against tumors expressing TCRβ. It is noted that T lymphocytes normally express the same receptors in lymphocyte migration and homing. Unexpectedly, and as will be more apparent from the following embodiments, it is believed that metastatic tumor cells mimic the equivalent functions of such lymphocytes as the metastatic tumor cells migrate to, and arrest and survive in, the sites of organs in which metastases develop.

Also disclosed by inventor Dr. Barberá in U.S. Pat. No. 5,536,642 is a detailed description of "prometastatic territories", the sites at which the metastasizing tumor cells arrest and survive in organs in which metastases develop. The prometastatic territories, as will be more apparent from the following embodiments, serve as a target so that any arrested metastatic tumor cells are then exposed to the chemotherapeutic agent, and/or the endothelial cells comprising the prometastatic territories are altered thereby inhibiting the ability of the metastatic tumor cells to arrest, survive, or proliferate in that site. Site-directed chemotherapy according to the present invention is directed to localizing targeted compositions to the prometastatic territories thereby directing therapy to metastatic colonies forming cells and/or to dormant metastatic tumor cells. Site-directed chemotherapy according to the present invention also encompasses, for primary non-lymphoid solid tumors having a high potential for metastasis (e.g., as predicted by IL-2Rα expression), "pre-treatment" of the prometastatic territories of the relevant organ in which metastases may develop as a preventative measure, e.g., to prevent the arrest and/or survival of any metastatic cells which may subsequently seed the organ.

Hematological malignancies, including leukemias and lymphomas, have been effectively treated by IL-2 fusion toxins which selectively bind and intoxicate cells bearing high affinity IL-2 receptors (LeMaistre et al., 1992, *Immunol-Res.*, 11, 42–53; and Waldmann et al., 1992, *Ann Intern Med.* 116:148–160); and by humanized antibodies to high affinity IL-2 receptors (hIL-2R), or anti-hIL-2R linked with toxins or radionuclides (Waldmann et al., 1992, supra). The method of the present invention for treating metastases of solid non-lymphoid tumors, and solid non-lymphoid tumors having a high probability of metastasis (i.e., expressing IL-2Rα), differs in several important respects. The haematological malignancies express hIL-2R (comprised of both α and β chains) which is efficiently bound by IL-2 and anti-hIL-2R. Further, by the nature of the malignancy, treatment with the IL-2-toxin or anti-hIL-2R-toxin or anti-hIL-2R, comprises infusion systemically. Since the present invention relies on the correlation, as shown in U.S. Pat. No. 5,536,642, between metastatic potential of a solid non-lymphoid tumor with expression of IL-2Rα, such non-lymphoid tumors expressing IL-2Rα have low affinity binding for IL-2-toxin or anti-hIL-2R-toxin or anti-hIL-2R. Thus, one embodiment of the method according to the present invention for anticancer therapy against metastases of solid non-lymphoid tumors, and solid non-lymphoid tumors having a high probability of metastasis, comprises administering a therapeutically effective amount of a chemotherapeutic agent comprising a targeting molecule linked to an antitumor agent wherein the targeting molecule is specific for (i.e. has high affinity binding to) IL-2Rα, such as humanized anti-IL-2Rα antibody or a monoclonal antibody, or a fragment thereof.

Despite IL-2Rα's low affinity for IL-2, a relatively small dose of IL-2 concentrated in the prometastatic territories will activate resting (e.g. dormant) metastatic tumor cells which makes them more susceptible to antitumor agents active against rapidly dividing cells. Thus, according to the method of the present invention, another embodiment for treating metastatic colony forming cells and dormant metastatic cells comprises simultaneous delivery of IL-2 and antitumor agent (wherein the antitumor agent or both the antitumor agent and IL-2 are linked to a targeting molecule) to the prometastatic territories. Note that this embodiment, and all other embodiments of the method according to the present invention do not comprise systemic administration, but rather comprise targeting the therapy directly to prometastatic territories. As will be described in more detail, controlled delivery of the site-directed chemotherapy is achieved by infusing, such as by a catheter or functionally similar means, the chemotherapeutic agent into one or more vascular accesses of the affected organ or site of the organ in which metastases may develop. The delivered chemotherapeutic agent then concentrates in the prometastatic territories of the organ by engaging its target via the targeting molecule portion of the chemotherapeutic agent.

EXAMPLE 1

This example illustrates characterization of the prometastatic territories. As will be more apparent, the prometastatic territories which are targeted by the site-directed chemotherapy of the present invention, may be identified by their vasculature, by the terminal sugar concentration, by preferential expression (a detectably higher concentration as compared to other endothelial cell subpopulations in the organ) of certain endothelial cell adhesion molecules expressed on the surface of the endothelial cells contained within the territory, and by the endothelial cell expression or lack of expression of cell factors such as cytokines and nitric oxide (NO). Metastatic cells of solid non-lymphoid tumors only colonize, and develop metastatic foci in a predictable location comprising unique capillary zones of the target organs such as liver and lung (Barberá-Guillem et al., 1989, *Cancer Research* 49:4003–4010; Barberá,-Guillem et al., 1992, *Int. J. Cancer Res.* 52:974–977; Barbera-Guillem et al., 1993, *Int. J. Cancer* 53:298–301; Barberá-Guillem et al., 1993, *Int. J. Cancer* 54:880–884). For example, in liver, the prometastatic territories are defined herein as being located in the 1st half (primarily in the second quadrant of that half) of the sinusoids extending from the portal vein to the hepatic vein. This area of the sinusoids is also known as the periportal segment or area of the sinusoids. In the lung, the prometastatic territories are defined herein as the terminal pre alveolar venules and the pleural terminal capillaries. Similar regions have been demonstrated in other organs including adrenal gland, brain, bone marrow, and lymph nodes.

Subpopulations of sinusoidal endothelial cells have been isolated and defined from organs in which metastases develop. For example, 2 specific subpopulations of liver sinusoidal endothelial cells, termed "type 1 endothelial cells" and "type 2 endothelial cells" have been isolated (Vidal-Vanachlocha et al., 1993, *Hepatology* 18:328–339). Type 1 endothelial cells display an identifying characteristic on their cell surface comprising preferentially expression of specific terminal sugars (N-acetyl galactosamine, GalNAC; and N-acetyl neuraminic acid, NANA), which is at least between 6 and 10 times higher concentration than that expressed by other cells residing in the capillary zones (see for example, Vidal-Vanachlocha et al., 1993, supra).

As will be more apparent from the following embodiments, the common factor of all characterized prometastatic territories is that the capillaries comprising the prometastatic territory contain a predominant and specific subpopulation of endothelial cells, type 1 endothelial cells, which are critical to the arrest and survival (collectively referred to as "colonization") of seeding metastatic tumor cells, and to their subsequent development into metastatic foci. The higher expression of specific sugars GalNAC and NANA results in preferential binding to type 1 endothelial cells by lectins that join specifically to those sugars when the lectin is injected in a circulatory site just prior to the prometastatic territory. Thus, in the present invention it is shown that the injected lectins having binding specificity for GalNAC and/or NANA, such as wheat germ agglutinin (WGA), are arrested, and practically abducted in the prometastatic territories. For example, illustrated in FIG. 1 are the zones of mammalian liver where tumor cells do not colonize and develop, therefore being visibly free of WGA tagged with rhodamine (dark areas); and zone 1 (functional description for the sinusoidal periportal area) containing predominately capillary type 1 endothelial cells comprising the prometastatic territories of the liver which are bound by WGA tagged with rhodamine (bright zones). Thus, the abduction of the lectin-fluorescent molecules occurs in the targeted area of the liver where metastatic tumor cells colonize, survive, and may subsequently further develop. The higher concentration of lectin contained in the capillaries comprising the prometastatic territories reflects the higher terminal sugar (GalNAC and GlcNAC) concentrations of capillary type 1 endothelial cells in these territories.

Figure 2A:
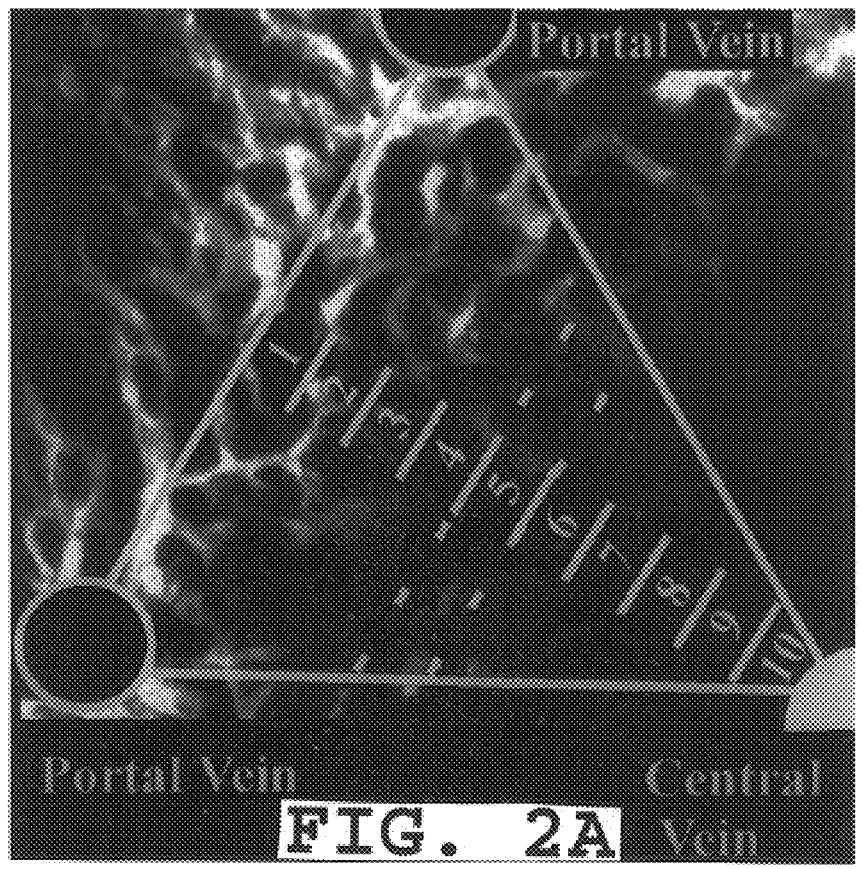
FIG. 2A is a photograph of a section of mammalian liver having designated thereon three functional zones located between a central vein and a portal vein, wherein zone 1 is the periportal area which comprises the prometastatic territory.
Figure 2B:
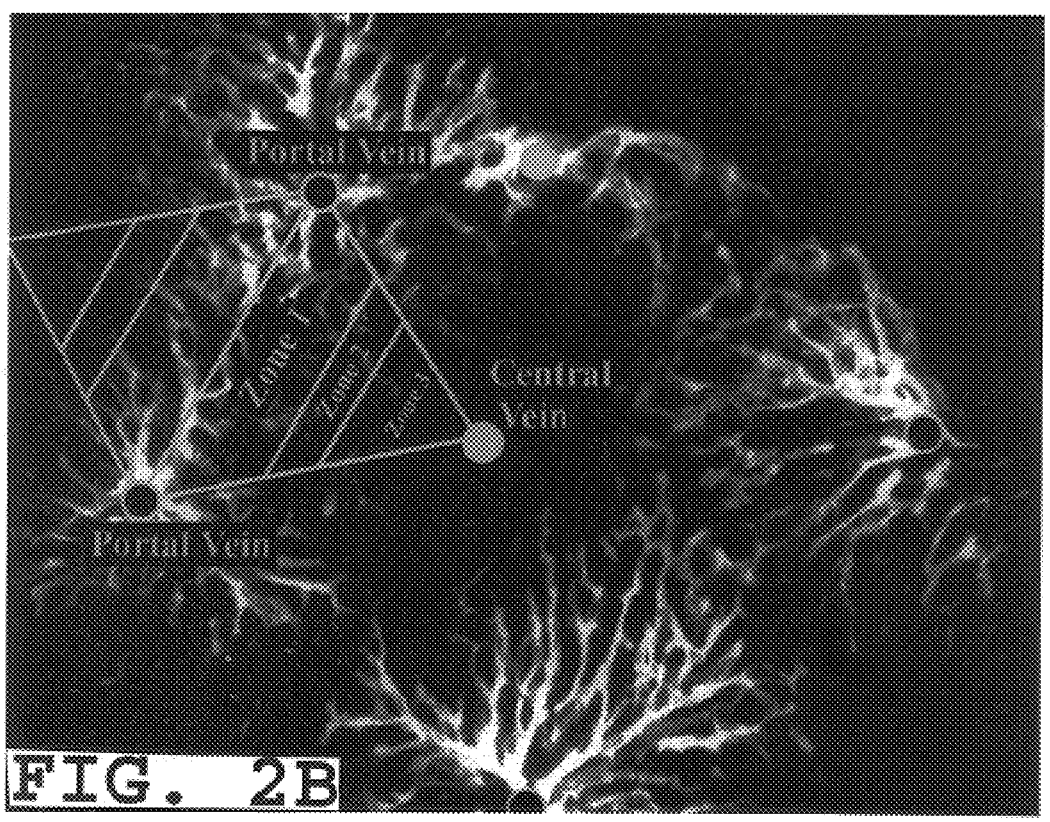
FIG. 2B is a photograph showing the three functional zones which are enlarged to illustrate subdomains.

An organ in which metastases may develop can be visualized as containing more than one functional zone. For example, FIG. 2A and 2B illustrate a section of a mammalian liver having designated three functional zones located between a central vein and portal veins. As shown in FIG. 2A, zone 1 is the periportal area which comprises the prometastatic territory. In the enlarged view shown in FIG. 2B, zone 1 is artificially subdivided by distance from the portal veins into subdomains 1–4, zone 2 is represented by subdomain 5, and zone 3 is represented by subdomains 6–10. Zone 2 and zone 3 can be described as being the perivenous and pericentral sinusoidal segments, respectively. As will be more apparent from the following embodiments, zone 1, zone 2, and zone 3 differ in the residing predominate endothelial cell type.

The relationship between the arrest of metastatic tumor cells and subsequent development into metastatic foci, and the areas in the organ in which metastatic foci are found, was determined essentially as described in Barberá-Guillem et al. (1989, *Cancer Res.* 49:4003–4010). Briefly, to determine arrest of metastatic cells, highly metastatic B16F10 melanoma cells ($5\times10^5$) were injected intrasplenically into mice. At 5 minute intervals in the first half hour postinjection, the treated mice (5 mice per each time point) were sacrificed; with the livers collected, frozen, sectioned, and histochemically stained (for succinate dehydrogenase activity) to determine in which areas of the histochemically stained hepatic tissue showed tumor cells (and the number of tumor cells). Assessment of the development of metastatic foci is essentially the same as for arrest of metastatic tumor cells, except that livers were harvested, fixed, and sectioned at day 7 postinjection. Liver sections were stained with hematoxylin and eosin, with the number of metastatic foci calculated by a stereological procedure, and the size of metastatic foci obtained using an integrated automatic image analysis system.

Figure 3:
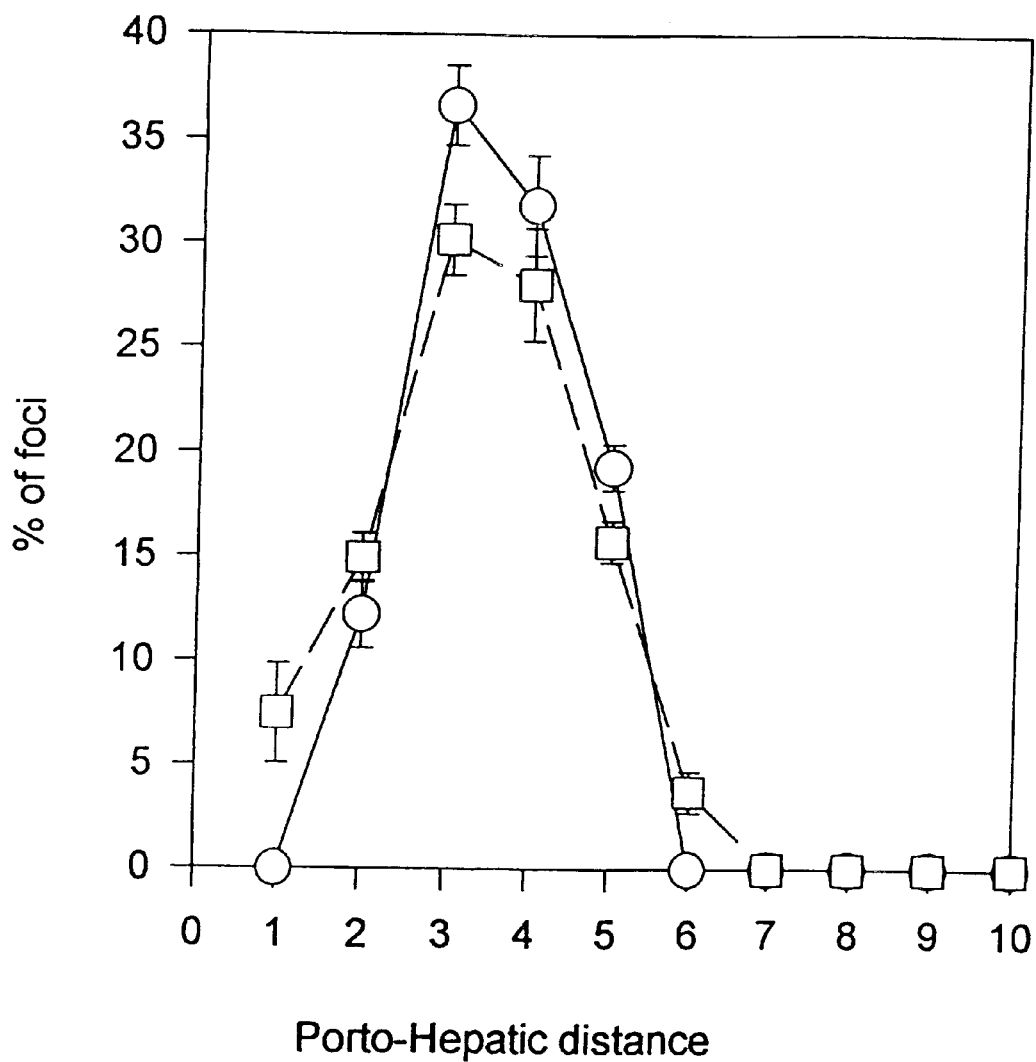
FIG. 3 is a graph depicting the relationship between zone 1 (designated by subdomains 1–4), zone 2 (designated by subdomain 5), and zone 3 (designated by subdomains 6–10) and the percentage of metastatic foci.

FIG. 3 is a graph depicting the relationship between zone 1 (designated by subdomains 1–4, as also illustrated in FIG. 2B), zone 2 (designated by subdomain 5), and zone 3 (designated by subdomains 6–10) and the percentage of metastatic foci. It is important to note that metastatic foci represent arrest and development of the initial seeding metastatic tumor cells. FIG. 3 illustrates that the vast majority of metastatic foci are found in zone 1 (e.g, in subdomains 2–4) Thus, it is demonstrated that metastatic tumor cells exhibit a biological predilection and specificity for arresting, surviving, and developing into metastatic foci in zone 1 (the prometastatic territories) of organs in which metastases develop.

EXAMPLE 2

This example illustrates isolation of type 1 endothelial cells found in the unique capillary zones comprising the prometastatic territories, and identification of this cell subpopulation as an endothelial cell subpopulation. Type 1 endothelial cells were isolated and purified as essentially taught by Vidal-Vanachlocha et al. (1993, supra, herein incorporated by reference). Basically, a portion of tissue from the organ in which metastases develops is enzymatically treated (e.g., pronase E and type 1 collagenase at concentrations of about 0.05%, and DNase (0.03%)) to achieve a cell suspension. The cell suspension is filtered through nylon, and washed and centrifuged several times, and treated (17.5% metrizamide) to remove cell debris and erythrocytes. An enriched population of type 1 endothelial cells was achieved by counterflow elutriation at 10° C. and 2,400 rpm with a flow rate of approximately 37 ml/minute. The collected cell fraction contained essentially type 1 endothelial cells (>90% of endothelial cells) together with Kupffer cells in a proportion of about 2:3. Further purification of the type 1 endothelial cells was achieved on discontinuous arabinogalactin density gradient centrifugation (containing densities of 1.02, 1.03, 1.04, and 1.06) at 20,000 rpm for 30 minutes at 25° C. Cells sedimenting in the 1.04 to 1.06 interphase were exclusively type 1 endothelial cells as characterized by more than 90% high-WGA binding. Using this procedure, for example, a yield of at least $4 \times 10^6$ type 1 endothelial cells can be obtained from 8 grams of organ tissue. Yields of type 1 endothelial cells may be improved by using the portal vein as tissue from which the cells are isolated, consistent with the anatomy of the location of type 1 endothelial cells.

It is noted here that it will be apparent from the further characterization of type 1 endothelial cells that follows, isolation and purification of type 1 endothelial cells may be facilitated at any stage by using one or more targeting molecules having affinity for cell surface receptors preferentially expressed by type 1 endothelial cells (as compared to expression by other cells in the area) as an immobilized affinity molecule in a process of affinity chromatography. The process of affinity chromatography is a standard technique known to those skilled in the art.

To identify and confirm that the isolated subpopulation comprising type 1 cells was endothelial cell in nature, subpopulations of type 1 endothelial cells and of type 2 endothelial cells were isolated and purified using the methods outlined above, and evaluated for expression of endothelial cell markers by nucleic acid amplification using commercially available primers specific for the endothelial cell markers. The endothelial cell markers included stem cell factor (SCF, see e.g., Koenig et al., 1994, Blood 83:2836–43), vascular endothelial cell growth factor receptor flt-1 (see, e.g., Mochida et al., 1996, Bichem. Biophys. Res. Commun. 226:176–9), von Willebrand factor (VW, see e.g., Gendron et al., 1996, Dev. Biol. 177:332–46), leukocyte inhibitory factor (LIF), and CD34 (Couvelard et al., 1996, Blood 87:4568–80). Other markers, that are not normally expressed in detectable levels in endothelial cells and which were evaluated as a control, included transforming growth factor beta (TGF-β), erythropoietin (EPO), interleukin-3 (IL-3), erythropoietin (EPO), macrophage colony stimulating factor (M-CSF), granulocyte colony stimulating factor (G-CSF), and vascular endothelial cell growth factor (VEGF). The results of the characterization of subpopulations of type 1 endothelial cells and of type 2 endothelial cells are shown in Table 1.

TABLE 1

| Cell marker | type 1 endothelial cells | type 2 endothelial cells |
|---|---|---|
| SCF | + | + |
| FLT- 1 | + | + |
| LIF | + | + |
| CD34 | + | + |
| TGF-β | − | − |
| EPO | − | − |
| G-CSF | − | − |
| M-CSF | − | − |
| IL-3 | − | − |
| VEGF | − | − |

Table 1 illustrates that certain cell markers (e.g., cytokines) expressed by endothelial cells are expressed by the subpopulation of type 1 cells thereby confirming that this subpopulation is of endothelial cell type.

EXAMPLE 3

This example illustrates characterization of unactivated endothelial cell type 1 comprising the predominate endothelial cell type in prometastatic territories. The following considerations may represent a useful basis for understanding the biological predilection and specificity of seeding metastatic tumor cells for arresting, surviving, and developing into metastatic foci in the prometastatic territories of organs in which metastases develop. As will be more apparent from the characterization that follows of the cell surface proteins expressed on the membrane of unactivated and/or activated type 1 endothelial cells, some of the seeding metastatic cells, circulating in an organ in which metastases develop, arrest in the prometastatic territories. The arrest of such metastatic cells in the prometastatic territories appears to be due to the local environment that type 1 endothelial cells provide, e.g. by expression of endothelial cell adhesion molecules or other cell surface receptors which (a) are preferentially expressed in higher amounts in zone 1 (as compared to the other sinusoidal areas of the organ), and (b) initially mediate the colonization of the seeding metastatic tumor cell to the endothelium comprising the prometastatic territories. Thus, in one embodiment of the method of the present invention for site-directed chemotherapy against metastases, such endothelial cell receptors present on unactivated type 1 endothelial cells are used as the target to which the chemotherapeutic agent is bound, thereby delivering and concentrating the chemotherapeutic agent to the area in which metastatic cells, if present, are colonized.

However, as will be more apparent from the characterization that follows of the proteins expressed by activated type 1 endothelial cells, initial colonization alone in the local environment provided by the unactivated type 1 endothelial cells is not enough for the seeding metastatic cells to develop into metastatic foci. The colonized metastatic tumor cells, by secreting their growth factors, interact directly with the type 1 endothelial cells and/or indirectly with neighboring or circulating cells (such as antigen presenting cells/Kupffer cells) which then secrete growth factors, in activating the type 1 endothelial cells. Activation of the type 1 endothelial cells appears responsible for the colonized metastatic tumor cells to subsequently develop into metastatic foci. Activated type 1 endothelial cells secrete growth factors that interact directly with the metastatic tumor and/or indirectly with neighboring or circulating cells (such as antigen presenting cells/Kupffer cells) which then secrete growth factors, thereby facilitating a local environment which stimulates the colonized metastatic tumor cells to subsequently develop into metastatic foci. A functionally similar regulatory network formed between lymphoid cells, hemopoietic cells, and endothelial cells has been described previously (Arai et al., 1990, *Rinsho Byori* 38:347–53). Thus, in another embodiment of the method of the present invention for site-directed chemotherapy against metastases, therapy is directed at either inhibiting activation of type 1 endothelial cells or by inhibiting the activity of growth factors secreted by the activated type 1 endothelial cells such that the local environment in which the metastatic cells are present does not stimulate the colonized metastatic tumor cells to subsequently develop into metastatic foci.

Cell Surface Marker Expression

For characterization and comparison, subpopulations of type 1 endothelial cells (predominate in the periportal segment of the organ sinusoids) and of type 2 endothelial cells (predominate in the perivenous segment of the organ sinusoids) were isolated and purified using the methods according to Example 2. Each subpopulation was evaluated for expression of endothelial cell surface markers including von Willebrand factor (VW), N-acetyl-glucosamine (GlcNAC), N-acetyl galactosamine (GalNAC), mannose receptor, receptors having albumin affinity, intra-cellular cell adhesion molecule-1 (ICAM-1), vascular cell adhesion molecule-1 (VCAM-1), platelet cell adhesion molecule-1 (PCAM-1), major histocompatibility antigen-II (MHC-II); and phagocyticability. VW was measured by immunofluorescence using a commercially available rabbit anti-human factor VIII antigen antibody. Essentially, a monolayer of either type 1 endothelial cells or type 2 endothelial cells were fixed with acetone-methanol-40% formalin, followed by washing with PBS. The cultures were incubated with the anti-human factor VIII antigen antibody for 40 minutes at 4° C. Fluorescence was measured by quantitative fluorescence microscopy (+=detectable fluorescence; −=absence of detectable fluorescence).

GlcNAC was measured by binding specificity with the lectin-wheat germ agglutinin (WGA). Viable type 1 endothelial cells and type 2 endothelial cells were separately assayed for GlcNAc expression by flow cytometry. First, each subpopulation was incubated in vitro at 37° C. for 5 minutes in the presence of fluorescein isoythiocyanate-labelled wheat germ agglutinin lectin (FITC-WGA, 10 $\mu$g/ml). Flow cytometric analysis was then performed using an argon laser, tuned at 488 nm, 250 mW, with a nozzle tip having an 80 mm diameter. Cells in each sample were simultaneously measured for forward light scatter, side scatter, and green fluorescence and red fluorescence emissions. The data was stored and analyzed using standard methods of analysis (see for example, Vidal-Vanachlocha et al. 1993, supra). The degree of lectin binding (and hence the degree of GlcNAC expression) was determined by the intensity of fluorescence and measured by semiautomatic evaluation. Alternatively, the degree of lectin binding was measured by quantitative fluorescence microscopy. "Very high" expression of GlcNAC, as compared to "very low" expression of GlcNAC, reflects at least a 4 fold to 6 fold increase in intensity of fluorescence.

Using methods similar to those used for measuring GlcNAC, GalNAC was measured by binding with lectin having specificity for GalNAC (e.g., *Dolichos biflorus, Vicia villosa, Wisteria floribunda, Sophora japonica*, peanut lectin, etc.; wherein += detectable fluorescence; −= absence of detectable fluorescence). Using methods similar to those used for measuring GlcNAC, mannose receptor was measured by incubation of the respective cell subpopulations with fluorescence-labeled ovalbumin (FITC-conjugated OA), and measurement by quantitative fluorescence microscopy of endocytosed FITC-conjugated OA which is proportional to mannose receptor expression (wherein high=visible fluorescence; and low=absence of visible fluorescence).

Endothelial cells contain membrane-associated polypeptides that bind Amadori-modified glycated albumin (GA), the predominant form of in which nonenzymatically glycated albumin exists in vivo, but do not bind to unmodified albumin. Viable type 1 endothelial cells and type 2 endothelial cells were separately assayed for expression of receptors having albumin affinity by flow cytometry. First, each subpopulation was incubated in vitro at 37° C. for 5 minutes in the presence of fluorescein isoythiocyanate labelled Amadori-modified glycated albumin (FITC-GA, 10 $\mu$g/ml). The cell subpopulations were then analyzed using flow cytometric analysis as described above (wherein high= detectable fluorescence; and low=absence of detectable fluorescence).

Endothelial cell adhesion molecules, and the integrin family to which they bind, are important for the colonization of hematopoietic cells, homing of lymphocytes, and proliferation of lymphocytes. Viable type 1 endothelial cells and type 2 endothelial cells were separately assayed for expression of ICAM-1, VCAM-1, and PCAM-1 by flow cytometry. First, each subpopulation was incubated in vitro at 4° C. for 40 minutes in the presence of saturating doses of either fluorescein isoythiocyanate labelled mouse monoclonal antibody against ICAM-1 (FITC-anti-ICAM-1), FITC-labelled anti-VCAM-1, or FITC-labelled anti-PCAM-1. The monoclonal antibodies used are commercially available. The cell subpopulations were then analyzed using the flow cytometric methods, data collection, and analysis as outlined above. For ICAM expression, "very high" represents a log of fluorescence intensity (e.g., $10^2$) greater than "low" expression (between $10^0$ and $10^1$). For VCAM, the expression by type 1 endothelial cells was similar to that by type 2 endothelial cells ("high to very high" is $10^1$ to $10^2$ log fluorescence intensity). For PCAM-1, (−) correlates with absence of detectable expression.

Major histocompatibility antigen-II (MHC-II) was measured by flow cytometry using fluorescent labeled monoclonal antibodies having binding specificity to MHCII. For MHC-II, (−) means absence of detectable expression. The ability of the respective endothelial cell subpopulations to engulf latex beads by phagocytosis was evaluated by utilizing commercially available fluorescent beads (0.5 micrometers in diameter) and flow cytometry to determine bead uptake as well as the number of beads per cell (see, e.g., Dunn and Tyrer, 1981, *J. Lab. Clin. Med.* 98:374–381; Doolittle, 1987, *Hepatology* 9:696–703). For phagocytic ability, (+) means presence of detectable activity; and (−) means absence of detectable activity.

The results of the characterization and comparison of cell surface molecules expressed by unactivated subpopulations of type 1 endothelial cells and by unactivated type 2 endothelial cells are shown in Table 2.

TABLE 2

| Cell surface molecule | type 1 endothelial cells | type 2 endothelial cells |
| --- | --- | --- |
| VW | + | + |
| GlcNAC | very high | very low |
| mannose receptor | high | low |
| affinity for GA | high | low |
| phagocytic ability | + | − |
| ICAM-1 | very high | low |
| VCAM-1 | high | very high |
| PCAM-1 | − | − |
| MHC-II | − | − |
| GalNAC | + | + |

Table 2 illustrates that certain cell surface molecules expressed on unactivated type 1 endothelial cells may be used as a target to which the chemotherapeutic agent may be directed. Thus in one embodiment of the method of the present invention for site-directed chemotherapy, cell surface molecules including GlcNAC, GalNAC, mannose receptor, polypeptides having binding affinity for GA, and ICAM-1 are preferentially expressed by unactivated type 1 endothelial cells (and also by activated type 1 endothelial cells), and may be used as targets for delivering and concentrating the chemotherapeutic agent to the area in which metastatic cells, if present, are colonized. This embodiment includes, for primary nonlymphoid solid tumors having a high potential for metastasis (e.g., as predicted by IL-2Rα expression), "pre-treatment" of the prometastatic territories of the relevant organ in which metastases may develop, as a preventative measure, e.g., to prevent the arrest and/or survival of any metastatic cells which may subsequently attempt to seed the organ.

Cytokine Expression

Subpopulations of unactivated type 1 endothelial cells and of unactivated type 2 endothelial cells were also characterized and compared for cytokine expression. Each subpopulation was isolated and purified using the methods according to Example 2, and then evaluated for the presence (+) or absence (−) of detectable expression of cytokines including stem cell factor (SCF), interleukin-1β (IL-1β), interleukin-3 (IL-3), interleukin-4 (IL-4), interleukin-6 (IL-6), interleukin-10 (IL-10), erythropoietin (EPO), thrombopoietin (TPO), macrophage colony stimulating factor (M-CSF), granulocyte colony stimulating factor (G-CSF), granulocyte-macrophage colony stimulating factor (GM-CSF), transforming growth factor beta (TGF-β), and interferon gamma (IFN-γ). The cytokine expression was evaluated by commercially available enzyme linked immunosorbent assays (ELISA) and performed using standard methods known to those skilled in the art (see, e.g., Endo et al., 1996, *Res. Commun. Mol. Pathol. Pharmacol* 94:23–38).

The results of the characterization and comparison of cytokines expressed by unactivated subpopulations of type 1 endothelial cells and by unactivated type 2 endothelial cells are shown in Table 3.

TABLE 3

| Cytokine | type 1 endothelial cells | type 2 endothelial cells |
| --- | --- | --- |
| SCF | + | + |
| IL-1β | + | − |
| IL-3 | − | − |
| IL-4 | − | − |
| IL-6 | − | + |
| IL-10 | + | + |
| EPO | − | − |
| TPO | + | + |
| M-CSF | − | − |
| G-CSF | − | − |
| GM-CSF | + | − |
| TGF-β | − | − |
| IFN-γ | + | + |

Table 3 illustrates that certain cytokines expressed on unactivated type 1 endothelial cells play a role in the survival of metastatic tumors cells after arrest in the prometastatic territories. More particularly, both IL-1β and GM-CSF secreted by type 1 endothelial cells may play a role in the cell maintenance of arrested metastatic tumor cells in zone 1, and thus may be used as a target to which the chemotherapeutic agent may be directed. In this regard, it was noted in the development of the present invention that metastatic tumor cells arresting in zone 3, the pericentral area of the organ in which metastases develop and which is deficient in type 1 endothelial cells, do not form colonies. In contrast, metastatic cells arresting in zone 1 remain and form colonies. Thus in another embodiment of the method of the present invention for site-directed chemotherapy, a therapeutically effective amount of an antagonist or inhibitor of IL-1β or GM-CSF are delivered as part of, or in conjunction with, the chemotherapeutic agent in the area in which metastatic cells, if present, are colonized. This embodiment includes, for primary nonlymphoid solid tumors having a high potential for metastasis (e.g., as predicted by IL-2Rα expression), "pre-treating" the prometastatic territories of the relevant organ in which metastases may develop, as a preventative measure, e.g., to prevent the arrest and/or survival of any metastatic cells which subsequently attempt to seed the organ. Inhibitors of IL-1β are known in the art and include, but are not limited to anti-IL-1β antibody (Troy et al., 1996, *Proc. Natl. Acad. Sci. USA* 93:5635–40), dexamethasone (Mullol et al., 1995, Clin. Exp. Allergy 25:607–15), and reactive oxygen intermediates (Sambo et al., 1996, *Blood* 87:1682–6). Antagonists of IL-1β are known in the art and include, but are not limited to IL-1β tripeptide antagonist (Hua et al., 1996, *J. Neuroscience* 16:4742–8), and IL-1 receptor antagonist (IL-lra, Troy et al., 1996, supra; Butler et al., 1995, *Eur. Cytokine Netw.* 1995, 6:225–230). Inhibitors of GM-CSF are known in the art and include, but are not limited to anti-GM-CSF antibody (Ohkawara et al., 1996, *J. Clin. Invest.* 97:1761–6), dexamethasone (Mullol et al., 1995, supra), prosta-glandin E2 (PGE2) and other cAMP elevating agents such as cholera toxin, forskolin, and isobutylmethylxanthine (Patil and Borch, 1995, *Blood* 85:80–6), IL-4 (Snoeck et al., 1993, *Leukemia* 7:625–9; Zhu and Atkinson, 1994, *Chin. Med. Sci. J.* 9:125–8), TGF-β (Alam et al., 1994, J. Exp. Med. 179:1041–5), and hydrocortisone (Kato and Schleimer, 1994, 172:113–24). Antagonists of GM-CSF are known in the art and include, but are not limited to GM-CSF antagonist mutant E21R (Iverson et al., 1996, *Proc. Natl. Acad. Sci. USA* 93:2785–9), and GM-CSF antagonist peptides (Monfardini et al., 1996, *J. Biol. Chem.* 271:2966–71).

Ability to Support Hematopoiesis

Two tumor markers, IL-2Ru and TCRO, are associated with metastasis as disclosed in U.S. Pat. No. 5,536,642, and are also hematopoietic cell surface markers. Other hematopoietic cell surface markers have been found to be expressed by metastatic cells of solid, nonlymphoid tumors (see for example, Patterson et al., 1985, *Am. J. Clin. Pathol.* 84:159–65; and Rusthoven et al., 1985, *Cancer* 56:289–93). It was noted in the development of the present invention that when metastatic tumor cells remain and form colonies in zone 1, such colonies resemble colony forming hematopoietic cells (CFC). It was then hypothesized that metastatic tumor cells and CFC share and respond to common growth factors and antigens. In this regard, the observation that the GM-CSF is preferentially secreted by type 1 endothelial cells and appears to facilitate colony formation of arrested metastatic cells is supported by the fact that GM-CSF can stimulate a single bone marrow stem cell to proliferate and differentiate into mature neutrophils, eosinophils, granulocytes, or macrophages (see for example, Fan et al., 1991, *In Vivo,* 5:571–7). To show an association between colony formation of metastatic cells and that of CFC, an experiment was performed to determine whether unactivated type 1 endothelial cells could support hematopoiesis in vitro by providing the microenvironment necessary for the maintenance and growth of hematopoietic cells. The same experiment was performed with unactivated type 2 endothelial cells for comparison purposes.

Type 1 endothelial cells and type 2 endothelial cells were isolated from murine liver using the methods according to Example 2. To obtain pure endothelial cell subpopulation cultures, type 1 endothelial cells were cloned by limiting dilution, and type 2 endothelial cells were also cloned by limiting dilution. There are several methods known to those skilled in the art to isolate and purify hematopoietic stem cells from various tissues (see, e.g., review by Visser and Van Bekkum, 1990, *Exp. Hematol.* 18:248–256). In this illustration, donors were pretreated with an agent (e.g., vinblastine, 5-fluorouracil, or hydroxyurea) to result in relative enrichment for the stem cells. More particularly, pluripotent hematopoietic stem cells were isolated from mice by pre-treating mice with 5-fluorouracil (5-FU) to increase the yield of stem cells; followed by isolation of Lin-, Sca+ cells (Nishio et al., 1996, *Stem Cells* 14:584–91; McNiece et al., 1990, *Int. J. Cell Cloning* 8:146–160; and Ogawa et al., 1991, *J. Exp. Med.* 174:63–71). Briefly, the animals were pre-treated with a single intraperitoneal injection of 5-FU at 150 mg/kg body weight. Bone marrow cells were harvested two days post-injection. This population of bone marrow cells includes primative multipotent precursors which are uncommitted cells expressing very early hematopoietic stem cell markers such as stem cell antigen (Sca), and the c-kit receptor, while having little or no expression of lineage marker (Lin). This population of bone marrow cells was resuspended in cell culture medium (Iscove's modified Dulbecco's medium) supplemented with 20% fetal calf serum and cultured in tissue culture dishes for 1 hour to remove adherent cells. The non-adherent bone marrow cells were removed and resuspended in the cell culture medium at $5 \times 10^5$ cells/ml. These non-adherent cells represent a population of hematopoietic stem cells from 5-FU treated mice.

Additionally, hematopoietic stem cells (Lin-, Sca+ cells) were isolated from normal mice (i.e., not treated with 5-FU) by immunomagnetic separation according to previously described methods (Spangrude et al., 1988, *Science* 241:58; 1990, *Exp. Hematol.* 18:920–23). Briefly, the bone marrow cells were incubated with a cocktail of antibodies having binding specificities for cell surface receptors including B220, GR-1, MAC-1, Lyt-2 (CD8), Ly-1 (CD5), L3T4 (CD4), and TER119. After washing the incubated cells, sheep anti-rat IgG(Fc) conjugated-immunomagnetic beads (commercially available) were added, and the mixture was incubated for 4° C. for 45 minutes. Cells bound to the magnetic beads were removed with a magnetic particle concentrator. Lin-cells recovered from the supernatant were incubated with either fluorescein isothiocyanate-conjugated rat anti-mouse Ly-6A/E antibody, or an isotype-matched control antibody. The cells were washed, and Lin-, Sca+ cells were isolated by cell sorting using a cell sorter. The final recovery of Lin-, Sca+ cells from unfractionated bone marrow cells was approximately 0.05% with a purity greater than 95%.

Having an isolated and purified subpopulation of type 1 endothelial cells, an isolated and purified subpopulation of type 2 endothelial cells, and two isolated and purified subpopulations of hematopoietic stem cells (one subpopulation from 5-FU treated mice, and one subpopulation from untreated mice), analyzed was the ability of either type 1 endothelial cells or type 2 endothelial cells to support in vitro hematopoiesis. That is, type 1 endothelial cells and type 2 endothelial cells were each tested for ability to induce proliferation, in the absence of exogenous hematopoietic growth factors, of hematopoietic stem cells isolated from 5-FU treated mice. Separate cultures of cloned type 1 endothelial cells, and of cloned type 2 endothelial cells, were maintained in cell culture medium (Iscove's modified Dulbecco's medium supplemented with 20% fetal calf serum). Hematopoietic stem cells isolated from 5-FU treated mice were inoculated ($1 \times 10^4$ cells/well) onto a confluent monolayer of type 1 endothelial cell culture or type 2 endothelial cell culture. Collagen-precoated control wells, to which the stem cells were added, included those containing tissue culture medium alone, or tissue culture medium with a combination of cytokines (stem cell factor (SCF) at 50ng/ml; IL-3 at 1 ng/ml; IL-6 at 10 ng/ml; and erythropoietin (EPO) at 5 U/ml). For each of the cocultures, half of the medium was collected every 5–7 days and replaced with the respective fresh medium.

Figure 4:
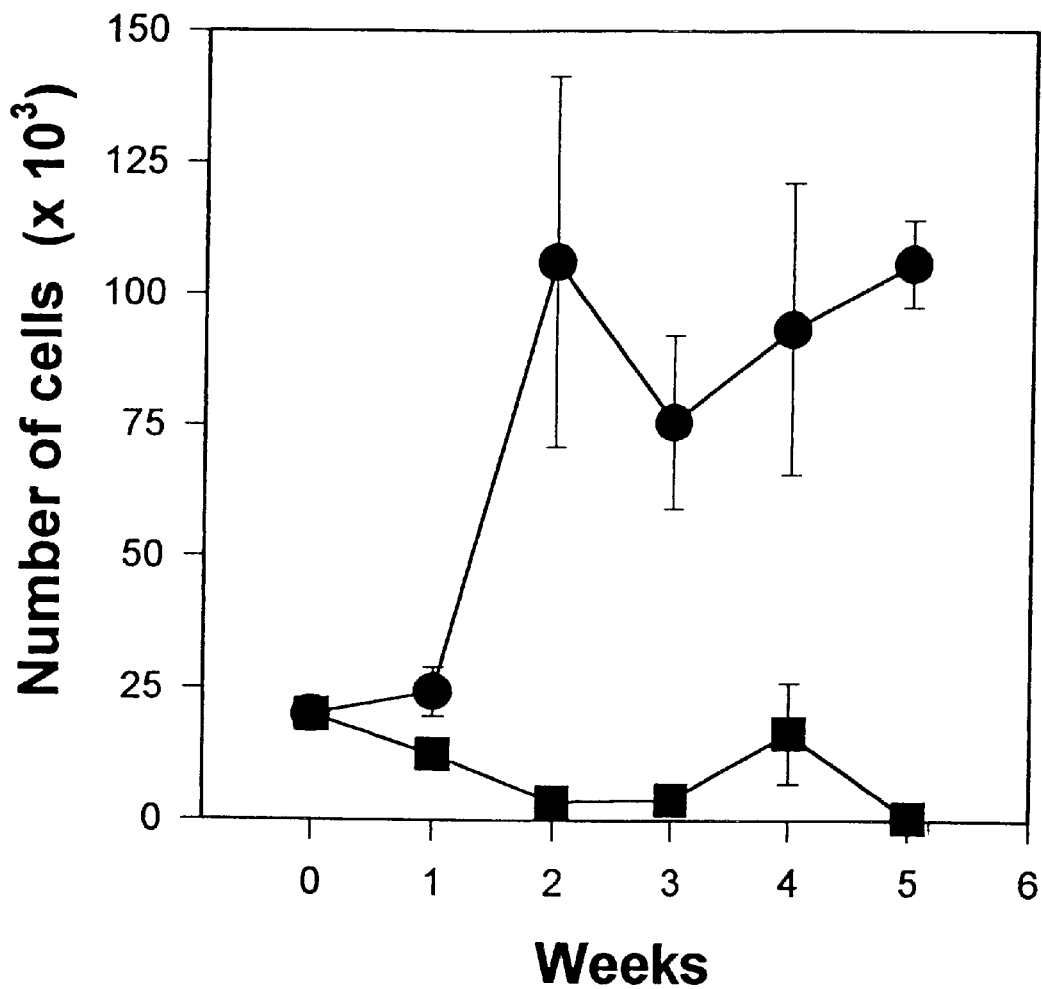
FIG. 4 is a graph illustrating the ability of either unactivated type 1 endothelial cells or unactivated type 2 endothelial cells to support hematopoiesis in vitro.

The number and viability of non-adherent cells present in the respective collected coculture medium were counted with a hemocytometer. After 21 days, the average count of non-adherent cells present in the type 1 endotheial cell coculture medium was 44,200±13,200; whereas the average count of non-adherent cells present in the type 12 endotheial cell coculture medium was 3,900±750. Thus, a statistically significant ($p<0.01$) increase of hematopietic cells was observed in the type 1 endothelial cell cocultures as compared to the type 2 endotheial cell cocultures. FIG. 4 illustrates that unactivated type 1 endothelial cells (●) can stimulate bone marrow stem cells to proliferate and differentiate into mature hematopoietic cells, and maintain the cells in culture for more than 5 weeks, when cultured together in vitro; whereas unactivated type 2 endothelial cells (■) do not support such hematopoiesis. Similar results were obtained using stem cells purified from untreated mice, suggesting that pretreatment with 5-FU did not significantly alter the ability of stem cells to respond to type 1 endothelial cells in coculture.

The proliferation of Lin-, Sca+ cells was also evaluated. Cytospin preparations of the non-adherent cells were stained with Giemsa solution for morphologic analysis. Aliquots of the non-adherent cells were incubated with conjugated monoclonal antibodies against murine cell surface receptors including B220, Gr-1, MAC-1, Lyt-2, Ly-1, L3T4, c-mpl, and ter119 for phenotypical analysis by flow cytometry (with data collection and analysis of fluorescent intensities). The main phenotype of the non-adherent cells in the type 1 endothelial cocultures consisted of 47% monocytes (MAC-1+), 33% granulocytes (Gr-1+), 16% megakaryocytes (c-mpl+), and low percentages (<5%) of erythroblasts (ter119+) and B cells (B220+).

Taken together, these results are evidence that type 1 endothelial cells can support hematopoiesis in vitro by providing the microenvironment necessary for the maintenance and growth of hematopoietic cells, as well as facilitating colony formation of metastatic cells after arrest in the prometastatic territories.

EXAMPLE 4

This example illustrates characterization of activated endothelial cell type 1 comprising the predominate endothelial cell type in prometastatic territories. Metastatic tumor cells arrested in the prometastatic territories can go into a dormant state, or form colonies in a slow proliferative state ("pseudo-resting"), wherein in each case the cells are highly resistant to NK cells and to antitumor agents that target rapidly dividing cells. Alternatively, metastatic tumor cells that have initially colonized in the prometastatic territories can enter a highly proliferative state in forming metastatic foci. Activation of the type 1 endothelial cells appears responsible for the colonized metastatic tumor cells to subsequently proliferate into metastatic foci. Type 1 endothelial cells are activated by cytokines (growth factors) causing the activated type 1 endothelial cells to secrete growth factors that interact directly with the metastatic tumor and/or indirectly with neighboring or circulating cells (such as antigen presenting cells/Kupffer cells) which then secrete growth factors, thereby facilitating a local environment which stimulates the colonized metastatic tumor cells to subsequently proliferate into metastatic foci. Thus, in another embodiment of the method of the present invention for site-directed chemotherapy against metastases, therapy is directed at either inhibiting activation of type 1 endothelial cells or by inhibiting the activity of growth factors secreted by the activated type 1 endothelial cells such that the local environment in which the metastatic cells are present does not stimulate the colonized metastatic tumor cells to subsequently proliferate into metastatic foci.

Cytokine Expression by Activated Type 1 Endothelial Cells

Cytokines causing the activation of type 1 endothelial cells, thereby facilitating a local environment which stimulates the colonized metastatic tumor cells to subsequently develop into metastatic foci, have been identified herein to include tumor necrosis factor alpha (TNF-α), IL-1β, and IFN-γ (acting separately, and also synergistically when in combination). To illustrate such activation, subpopulations of unactivated type 1 endothelial cells and of unactivated type 2 endothelial cells were activated by TNF-α, and then characterized and compared for cytokine expression. Each subpopulation was isolated and purified using the methods according to Example 2. Cultures of each subpopulaton were treated for four hours with 25 ng/ml TNFα at 37° C. The TNFU was then removed by washing the TNFα-activated cells. As controls, in parallel experiments, respective cytokine expression was quantitated in unactivated type 1 endothelial cells and unactivated type 2 endothelial cells. The activated endothelial cells were then evaluated by commercially available ELISAs for quantitating the expression of cytokines including IL-1β, IL-2, IL-4, IL-6, IL-10, GM-CSF, IFN-65, and TNF-α.

Figure 5A:
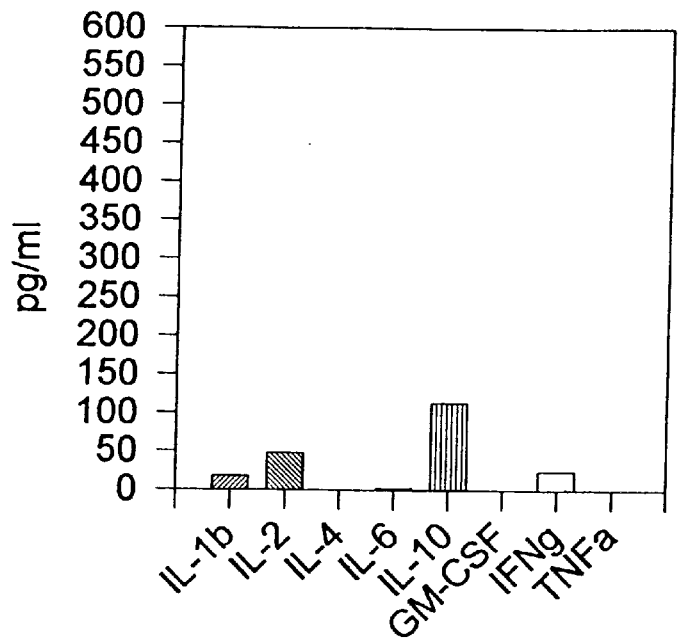
FIG. 5A is a bar graph illustrating the cytokine expression of unactivated type 1 endothelial cells.
Figure 5B:
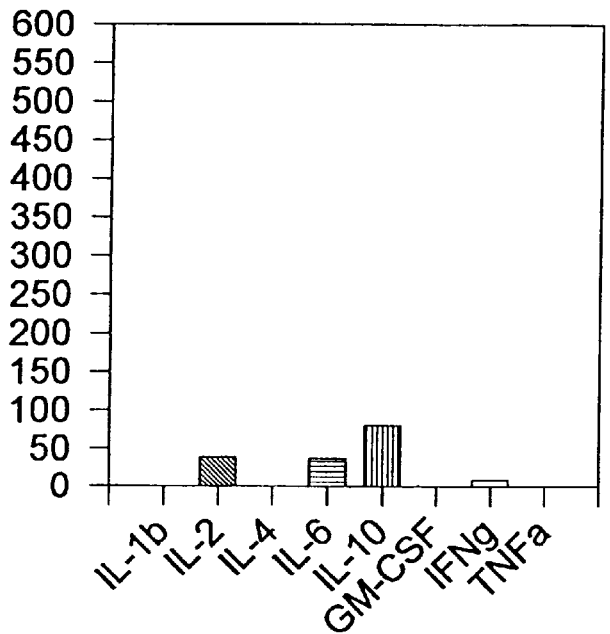
FIG. 5B is a bar graph illustrating the cytokine expression of unactivated type 2 endothelial cells.
Figure 5C:
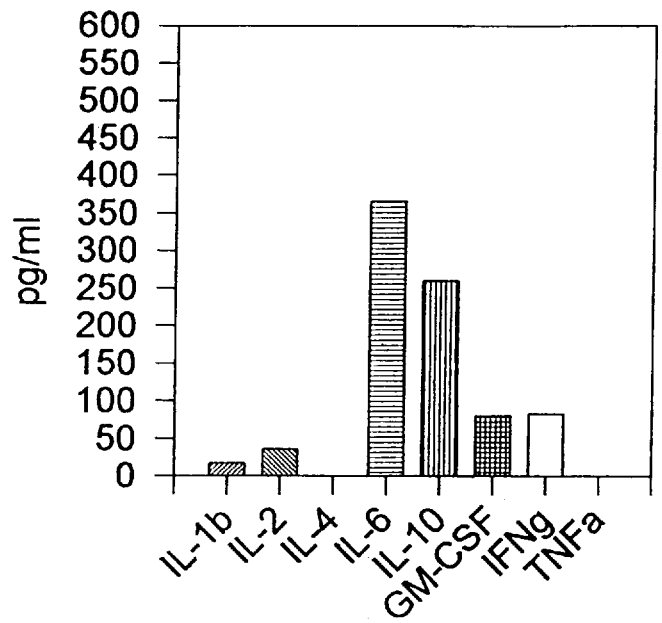
FIG. 5C is a bar graph illustrating the cytokine expression of type 1 endothelial cells activated by TNF-α.
Figure 5D:
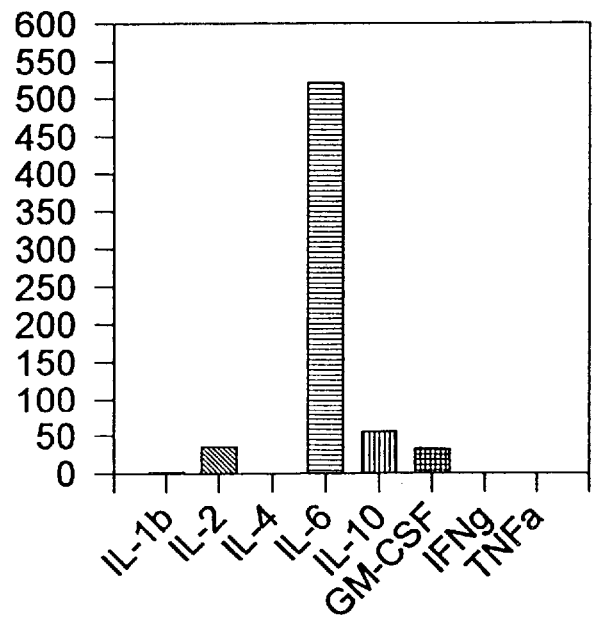
FIG. 5D is a bar graph illustrating the cytokine expression of type 2 endothelial cells activated by TNF-α.

FIG. 5 illustrates the comparison of cytokine expression (measured as pg/ml) between unactivated type 1 endothelial cells (FIG. 5A), unactivated type 2 endothelial cells (FIG. 5B), type 1 endothelial cells activated by TNF-α (FIG. 5C), and type 2 endothelial cells activated by TNF-α (FIG. 5D). Similar cytokine expression was observed when type 1 endothelial cells were activated with either IL-1β or IFN-γ. More particularly, IL-6 and high concentrations of IL-10 secreted by activated type 1 endothelial cells may facilitate a local environment which stimulates the colonized metastatic tumor cells to subsequently develop into metastatic foci, and thus may be used as a target to which the chemotherapeutic agent may be directed. In that regard, IL-6 has been shown to mediate autocrine and paracrine growth of multiple myeloma cells (Urashima et al., 1996, *Blood* 88:2219–27). Additionally, from this data it appears that metastatic cells, to form metastatic foci in organs, use the same signal for cell proliferation as organ cells use in regenerative processes: TNFα-induced IL-6 (see, e.g., liver regeneration, Michalopoulos and DeFrances, 1997, *Science* 276:60–66). While IL-10 has been reported to inhibit tumorigenicity through an NK-cell dependent mechanism (Zheng et al., 1996, *J. Exp. Med.* 184:579–84), high concentrations of IL-10 have been reported to inhibit macrophage release of reactive oxygen intermediates, thereby making conditions more permissive of tumor cell growth (Bogdan et al., 1991, *J. Exp. Med.* 174:1549–55). Further, IL-10 has been shown to inhibit antigen presentation to human tumor-specific and allospecific cytotoxic lymphocytes (Salaza-Onfray et al., 1995, *J. Immunol.* 154:6291–8).

Thus, another embodiment of the method of site-directed chemotherapy of the present invention is to inhibit the cytokine activity of growth factors IL-6 and IL-10 secreted by the activated type 1 endothelial cells, such that the local environment in which the metastatic cells are present does not stimulate the colonized metastatic tumor cells to subsequently develop into metastatic foci. Inhibition of such activities of IL-6 and IL-10 may be achieved by delivering a therapeutically effective amount of an antagonist or inhibitor of IL-6 and/or of an antagonist or inhibitor of IL-10 as part of, or in conjunction with, the chemotherapeutic agent in the area in which metastatic cells, if present, are colonized; and/or to inhibit or prevent activation by TNF-α, IL-1β, or IFN-γ of type 1 endothelial cells.

In that regard, inhibitors of IL-6 are known in the art and include, but are not limited to, anti-IL-6 monoclonal antibodies (Urashima et al., 1996, supra), cyclosporin A (Yamamura et al., 1996, *Leukemia* 10:1504–8), tenidap (Husebekk and Stenstad, 1996, *Scand. J. Immunol.* 43:551–5), 4-deoxy-pyridoxine (Frydas et al., 1996, *Immunol. Lett.* 49:179–84), and nordihyroguiaretic acid (Esa and Converse, 1996, *Scand. J. Immunol.* 43:127–33). Antagonists of IL-6 are known in the art and include, but are not limited to, IL-6 receptor antagonists (Demartis et al., 1996, *Cancer Res.* 56:4213–8), IL-6 dimers (Ward et al., 1996, *J. Biol. Chem.* 271:20138–44), IL-6 variants (Sporeno et al., 1996, *Blood* 87:4510–19), and activin A (Brosh et al., 1995, *J. Biol. Chem.* 270:29594–600). Inhibitors of IL-10 are known in the art and include, but are not limited to, anti-IL-10 antibody (Kimata et al., 1996, *J. Exp. Med.* 184:357–64), and vasoactive intestinal peptide (Martinez et al., 1996, *J. Immunol.,* 156:4128–36). Antagonists of IL-10 are known in the art and include, but are not limited to, IL-10 receptor antagonists, and human autoantibodies to IL-10 (Menetrier-Caux et al., 1996, *Clin. Exp. Immunol.* 104:173–9).

Alternatively, another embodiment of the method of site-directed chemotherapy of the present invention is to inhibit or prevent activation of the type 1 endothelial cells by delivering a therapeutically effective amount of an antagonist or inhibitor of IL-1β, and/or of an antagonist or inhibitor of TNF-α, and/or of an antagonist or inhibitor of IFN-γ, as part of, or in conjunction with, the chemotherapeutic agent in the area in which metastatic cells, if present, are colonized. Inhibitors of, or antagonists of IL-1β are known in the art, and examples have been detailed above. Inhibitors of TNF-α are known in the art and include, but are not limited to, drugs including tenidap (Husebekk and Stenstad, 1996, supra), sarcophtol A or canventol or tomaxifen (Suganuma et al., 1996, *Cancer Res.* 56:3711–5), antiinflammatory agents (Cottam et al., 1996, *J. Med. Chem.* 39:2–9), anti-TNF-α antibody (Edwards et al., 1996, *J. Immunol.* 157:1758–72; chimeric antibody- Walker et al., 1996, J. Infect. Dis. 174:63–68; monoclonal antibody- Rabinovici et al., 1996, *Circ. Res.* 78:329–36), arachidonic acid (Stuhlmeier et al., 1996, *Eur. J. Immunol.* 26:1417–23), immunosuppressive agents (Sekine-Okano et al., 1996, *Invest. Ophthmalol. Vis. Sci.* 37:1302–10), thalidomide (Klausner et al., 1996, *J. Acquir. Immune Defic. Syndr. Hum. Retrovirol.* 11:247–57), BMS-182123 (Warr et al., 1996, *J. Antibiot.* 49:234–40), and oils rich in n-3 fatty acids (Caughey et al., 1996, *Am. J. Clin. Nutr.* 63:116–22). Antagonists of TNF-α are known in the art and include, but are not limited to, TNF-α receptor antagonists, soluble TNF-α receptors (e.g., types 1, II, and III; Creange et al., 1996, *J. Neuroimmunol.* 68:95–9; Moldawer, 1993, *Blood Purif.,* 11:128–33), soluble fragment of TNF-α receptor (Takahashi et al., 1996, *J. Sleep Res.* 5:106–14), TNF-α-antagonist monoclonal antibody (Corti et al., 1994, *Lymphokine Cytokine Res.* 13:183–90) and TNF-β (Oster et al., 1987, *Blood* 70:1700–03). Inhibitors of IFN-γ are known in the art and include, but are not limited to, thalidomide (McHugh et al., 1995, *Clin. Exp. Immunol.* 99:160–7), anti-IFN-γ antibodies (Caruso et al., 1994, *J. Interferon Res.* 14:161–4), tetanus toxin (Pitzurra et al., 1993, *FEMS Immunol. Med. Microbiol.* 7:289–95), and IL-4 (Miossec, 1994, J. Interferon Res. 14:285). Antagonists of IFN-γ are known in the art and include, but are not limited to, IFN-γ receptor monoclonal antibodies (Bridges et al., 1995, *Mol. Immunol.* 32:1329–38), and IFN-γ receptor homologs (Mossman et al., 1995, *J. Biol. Chem.* 270:3031–8).

EXAMPLE 5

This example illustrates further characterization of activated endothelial cell type 1 comprising the predominate endothelial cell type in prometastatic territories. As described above, certain cytokines including TNF-α, IL-1β, and IFN-γ, activate type 1 endothelial cells to secrete factors which facilitate a local environment which stimulates the colonized metastatic tumor cells to subsequently develop into metastatic foci. However, it has also been determined in the present invention that unactivated or activated type 1 endothelial cells fail to secrete certain factors that have tumoricidal activity. Thus, another embodiment of the method of site-directed chemotherapy of the present invention is to induce type 1 endothelial cells to secrete factors having tumoricidal activity.
NO Production For example, nitric oxide (NO) is a molecule formed in cells from L-arginine residues by the enzyme nitric oxide synthase (NO synthase). The role of NO in macrophage tumoricidal activity is known to those skilled in the art. A number of cytokines have been shown to induce NO from a variety of cells types. For example, certain cytokines including TNF-α and IFN-γ can each induce nitric oxide synthesis in rodent macrophages exposed to the cytokine (Alder et al., 1994, Biochem. *Biophys. Res. Commun.* 198:510–515). However, in bovine bone-marrow derived macrophages, these cytokines alone induce little NO. Rather, a combination of these cytokines with bacterial lipopolysaccharide is needed to induce NO production in bovine bone-marrow derived macrophages. Induction of NO in mammalian vessel endothelial cells has also been shown (Shuler et al., 1995, *J. Leukoc. Biol.* 57:116–21; Inoue et al., 1995, *Arteriorscler. Thromb. Vasc. Biol.* 15:1255–61). Thus, if type 1 endothelial cells do not produce NO, an important means of tumoricidal activity would then be absent in the prometastatic territories.

To investigate whether subpopulations of activated type 1 endothelial cells and of activated type 2 endothelial cells produce NO, each subpopulation was activated by either TNF-α, IFN-γ, or a combination of TNF-60 and IFN-γ, and then characterized and compared for NO expression. Each subpopulation was isolated and purified using the methods according to Example 2. Cytokine induced-activation was performed using the methods according to Example 4. The supernatants from type 1 endothelial cell cultures and from type 2 endothelial cell cultures were assayed for NO production according to previously described methods for determining NO (Kolb et al., 1994, *J. Biol. Chem.* 269:9811–9816; Viinikka, 1996, *Scand. J. Clin. Lab. Invest.* 56:577–81). Briefly, cell-free supernatants (50 μl) were transferred into wells of a 96 well microtiter plate containing per well 100 μl Griess reagent (1% sulfanilamide in 30% acetic acid and 0.5% of N-1-naphtylethylenediamine dihydrochloride in 60% acetic acid). The mixture was incubated for 10 minutes at 25° C., and the product of the reaction was detected by absorbance at 540 nm using a precision microplate reader. The concentration of nitrite was calculated by comparison with standard concentrations of sodium nitrite. Concentrations of nitrite/nitrate are typically used in the art as quantitative indices of NO production.

Figure 6:
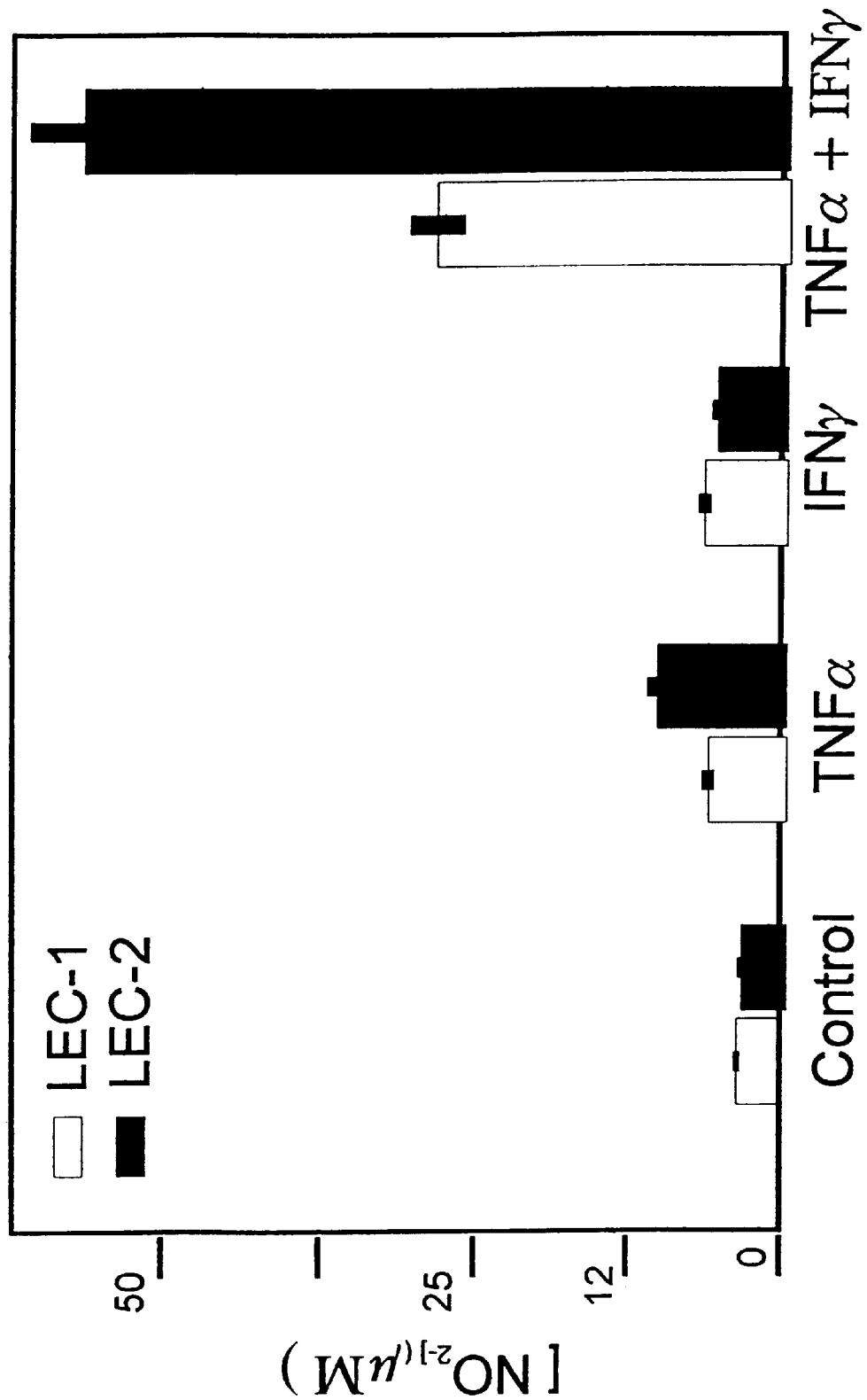
FIG. 6 is a bar graph illustrating the comparison of nitric oxide production (measured as $NO_2$) in unactivated type 1 endothelial cells, unactivated type 2 endothelial cells, and type 1 endothelial cells or type 2 endothelial cells activated by either TNF-α, or IFN-γ, or by a combination of TNF-αand IFN-γ.

FIG. 6 illustrates the comparison of NO production (measured as $NO_2$ in micromoles-μM) in unactivated type 1 endothelial cells (control □), unactivated type 2 endothelial cells (control ■), type 1 endothelial cells activated by TNF-α (TNF-α□), type 2 endothelial cells activated by TNF-α (TNF-α□), type 1 endothelial cells activated by IFN-γ (IFN-γ□), type 2 endothelial cells activated by IFN-γ (IFN-γ□), type 1 endothelial cells activated by a combination of TNF-α and IFN-γ (TNF-α+IFN-γ□), and type 2 endothelial cells activated by TNF-α and IFN-γ (TNF-α+IFN-γ□). As shown in FIG. 6, very little $NO_2$ is constitutively produced in either unactivated type 1 endothelial cells or unactivated type 2 endothelial cells. Also, little induction (as measured by $NO_2$) is observed in type 1 endothelial cells or type 2 endothelial cells when activated by either TNF-α or by IFN-γ. In contrast, activation of type 2 endothelial cells by a combination of TNF-α and IFN-γ resulted in significant amounts (e.g., >50 μM) of $NO_2$ produced by such activated type 2 endothelial cells.
Endothelial Cell NO-mediated Tumoricidal Activity This initial characterization of NO production in these endothelial cell subpopulation suggests that another reason why metastatic cells do not survive in zones 2 and 3, where the predominate endothelial cell type is type 2 endothelial cells, is that the $NO_2$ production by activated type 2 endothelial cells is in sufficient amounts to mediate tumoricidal activity. Endothelial cell NO-mediated tumoricidal activity in prometastatic territories (or in type 1 or type 2 endothelial cells) has not been described previously. Using the methods according to Examples 2 and 4, to investigate whether NO produced by either type 1 or type 2 endothelial cells has tumoricidal activity, each subpopulation was first activated with TNF-α (5 ng/ml) and then assessed for the ability to mediate tumor cell killing when mixed with tumor cells. To confirm that any tumoricidal activity observed was due to $NO_2$ production, parallel experiments were performed in which the endothelial cell subpopulation was treated with NG-monomethyl-L-arginine (LNMA) during incubation with tumor cells. LNMA is a NO synthase inhibitor which specifically inhibits NO formation (see, e.g., Shuler et al., 1995, supra).

Figure 7:
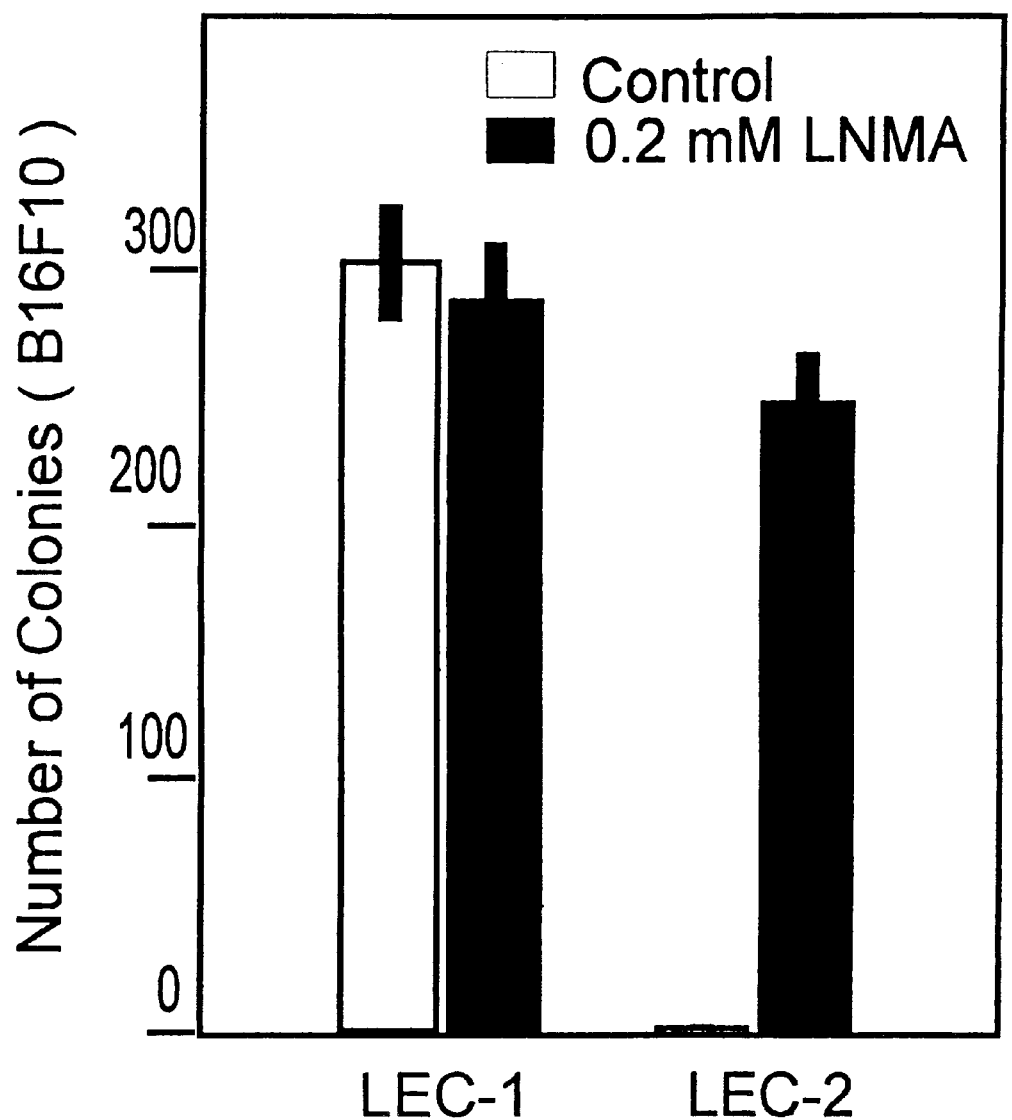
FIG. 7 is a bar graph illustrating the relation between amount of NO production in type 1 endothelial cell and type 2 endothelial cell populations, and tumoricidal activity (as measured by tumor colony formation).

FIG. 7 illustrates the relation between NO production in type 1 endothelial cell and type 2 endothelial cell populations, and tumoricidal activity (as measured by tumor colony formation). Activated type 1 endothelial cells (FIG. 7, LEC-1 □), lack the ability to inhibit tumor colony formation. Treatment of activated type 1 endothelial cells with LNMA does not significantly change the lack of tumoricidal activity exhibited by the activated type 1 endothelial cells (FIG. 7, LEC-1 ■). This would be an expected result because type 1 endothelial cells do not produce NO in an amount or form which is effective in tumoricidal activity. In contrast, activated type 2 endothelial cells are very effective in inhibiting tumor growth, e.g. in tumoricidal activity (FIG. 7, LEC-2 □), and their ability to mediate tumoricidal activity is significantly inhibited by LNMA, a NO synthase inhibitor which specifically inhibits NO formation (FIG. 7, LEC-2 ■).

Accordingly, the ability to produce NO in an amount which is effective in tumoricidal activity is an important mechanism by which endothelial cells prevent metastases from developing in organs in which metastases develop. It is interesting to note that prolonged nitrous oxide ($NO_2$) exposure has also been shown to suppress hematopoiesis by impairing the hematopoietic inductive microenvironment and hematopoietic cells in the spleen and bone marrow (Suzuki et al., 1990, *Anesth. Analg.* 71:389–393). Further, the failure of type 1 endothelial cells to produce NO in an amount which effects tumoricidal activity directly affects colonization of metastatic tumor cells, and development into metastatic foci. Additionally, impairment of endothelial function, specifically inhibition of NO synthase, has also been shown to induce tissue hypoxia (Pohl et al., 1993, *Eur. Heart J.*, 14:93–8). Tissue hypoxia is known to drive tumors and other cells to generate angiogenic molecules, such as to generate new microvasculature necessary for tumor growth (see, e.g., Battegay, 1995, *J. Mol. Med.* 73:333–46). Further, certain antitumor agents (e.g., antiangiogenic agents), but not all antitumor agents, appear to effect increased therapeutic response when hypoxia is decreased (Teicher et al., 1995, *In Vivo,* 9:11–8). Therefore, the inability of type 1 endothelial cells to produce nitric oxide appears to be important in providing an environment in which metastatic cells can colonize and develop into foci; and further may affect the efficacy of treatment with certain types of antitumor agents.

These results indicate that production of NO appears to be repressed or inhibited in type 1 endothelial cells, and such repression or inhibition may be a target for therapeutic intervention. In that regard, the following should be considered. There are multiple forms of the gene encoding the nitric oxide synthase. For example, a form of the gene (iNOS; NOS-2; or "type II") has its expression inducible by cytokines (e.g., TNF-α and/or IFN-γ) separately or in combination with bacterial lipopolysaccharide. Note that type 1 endothelial cells, when activated by TNF-α and/or IFN-γ, fail to show an induction in expression of iNOS. This suggests that induction of iNOS by these cytokines is being inhibited. It is also important to note that, as shown in FIG. 5, activated type 1 endothelial cells produce a significant amount of IL-10. IL-10 suppresses induction of iNOS (Modolell et al., 1995, *Eur. J. Immunol.* 25:1101–4). Thus, treatment of type 1 endothelial cells with a therapeutically effective amount of an antagonist or inhibitor of IL-10 may allow for induction of iNOS and subsequent production of NO to an amount effective for tumoricidal activity.

Another isoform of NO synthase (eNOS or NOS-3) is constitutively expressed in human endothelial cells (Tang et al., 1995, *Biochem. Biophys. Res. Commun.* 213:673–80). Hypoxia decreases NOS-3 mRNA expression and production of NOS-3 protein, resulting in reduction of NO production by human endothelial cells (Ziesche et al., 1996, *Proc. natl. Acad. Sci. USA* 93:12478–83). The combination of hypoxia with IL-1β or TNFα augments the reduced production of NO by human endothelial cells (Ziesche et al., 1996 supra). Thus, treatment of type 1 endothelial cells with therapeutically effective amount of an antagonist or inhibitor of IL-1β and/or TNF-α (as described above) may also allow for induction of NOS-3 and subsequent production of NO to an amount effective for tumoricidal activity. It is also interesting to note that the combination of hypoxia with IL-10 or TNFα superinduces the expression of IL-6 in human endothelial cells (Ziesche et al., 1996 supra).

Therefore, another embodiment of the method of site-directed chemotherapy of the present invention is to treat type 1 endothelial cells with a thrapeutically effective amount of an inducer of NO production to effect production of NO and secretion of $NO_2$ in an amount effective in mediating tumoricidal activity thereby preventing colonization and/or subsequent development into metastatic foci. In one illustration of this embodiment, in type 1 endothelial cells the inhibition or repression of the induction of isoforms of NOS is overcome by treating type 1 endothelial cells with an inducer of NO production. An inducer of NO production can be selected from the group consisting of a drug that induces expression of NOS (e.g., holo-transferrin: Takenaka et al., 1995, *Biochem Biophys. Res. Commun.* 213:608–15; and pteridine compounds, e.g., neopterin: Hoffman et al., *FEBS Lett.* 391:181–4), a cytokine that induces expression of NOS, introducing multiple copies of an NOS gene into human type 1 endothelial cells, an antagonist or inhibitor of IL-1β, an antagonist or inhibitor of TNF-α, an inhibitor or antagonist of transforming growth factor-beta 1 (TGF-β1; Inoue, et al., 1995, *Arterioscler. Thromb. Vasc. Biol.* 15:1255–61), and an antagonist or inhibitor of IL-10 (examples provided above), in sufficient amounts to thereby overcome repression or inhibition of NO production wherein NO is produced in sufficient amounts by the treated type 1 endothelial cells to mediate tumoricidal activity.

Introduction of an NOS gene is one illustration of the embodiment of the method of site-directed chemotherapy of the present invention in which type 1 endothelial cells are treated to produce NO and secrete $NO_2$ in an amount effective in mediating tumoricidal activity thereby preventing colonization and/or development into metastatic foci. In this illustration, a vector containing a gene encoding NO synthase is introduced into type 1 endothelial cells such that the gene is either constitutively expressed or is induced to produce NOS, resulting in subsequent production of sufficient levels of NO to mediate tumoricidal activity. The respective genes for human endothelial NOS isoforms NOS-2 and NOS-3, and for the neuronal isoform (NOS-1) have been cloned, isolated, and characterized (see, e.g., Miyahara et al., 1994, *Eur. J. Biochem.* 223:719–726; Wang and Marsden, 1995, *Curr. Opin. Nephrol. Hypertens.* 4:12–22; Xu et al., 1996, *Biochem. Biophys. Res. Commun.*

219:784–8; and Nadaud et al., 1994, *Biochem. Diophys. Res. Commun.* 198:1027–33). Further, all three isoforms have been cloned into vectors, and have been successfully transferred into, and expressed in, vascular endothelial cells (Channon et al., 1996, *Cardiovasc. Res.* 32:962–72; Tang et al., 1995, supra; Janssens et al., 1996, *J. Clin. Invest.* 98:317–24; Tzeng et al., 1996, *Mol. Med.* 2:211–25). Expression vectors used included retroviral vectors, and adenoviral vectors. Thus, using molecular methods known to those skilled in the art, and using the site-directed delivery according to the present invention, a vector containing a gene encoding an isoform of NOS operatively linked to a promoter is introduced into type 1 endothelial cells in vivo thereby allowing for expression of NOS, and subsequent production of sufficient levels of NO to mediate tumoricidal activity in the prometastatic territories. In this regard, it is also noted that activated type 1 endothelial cells have upregulated receptor-mediated endocytosis such as via the mannose receptor. Since activated type 1 endothelial cells are very active in endocytosis via the mannose receptor, such cells are easily transfectable using methods and compositions known to those skilled in the art for transfecting via the mannose receptor, including but not limited to, liposomes wherein the liposomes encapsulate the NOS expression vector, and having mannose incorporated in the membrane of the liposome such that it is accessible to interact with the mannose receptors present on the type 1 endothelial cells. Alternatively, as noted above, type 1 endothelial cells (unactivated or activated) are sensitive to adenovirus type 3 infection, and thus may be infected with an adenoviral vector for the expression of NOS.

Figure 8:
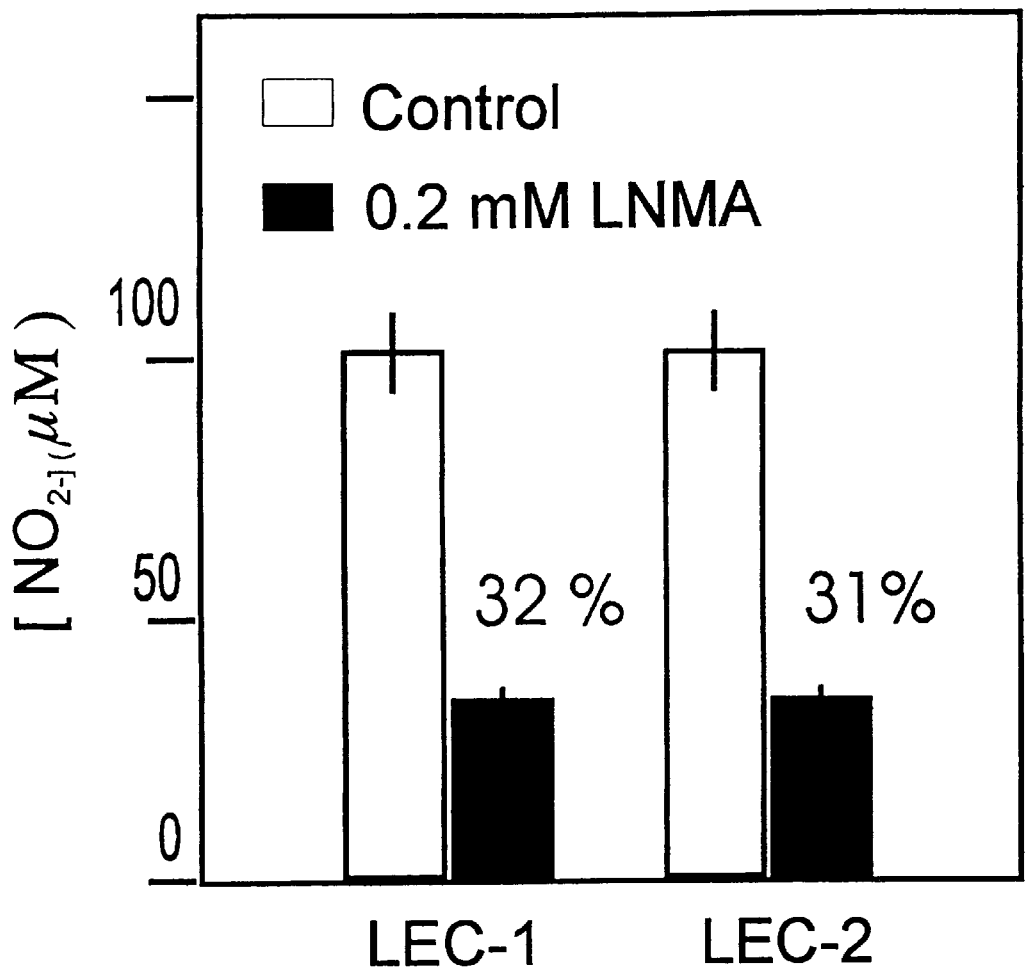
FIG. 8 is a bar graph illustrating the comparison of nitric oxide production (measured as $NO_2$) in type 1 endothelial cells transfected to produce iNOS; the transfected cells treated with LNMA; activated type 2 endothelial cells; and activated type 2 endothelial cells treated with LNMA.
Figure 9A:
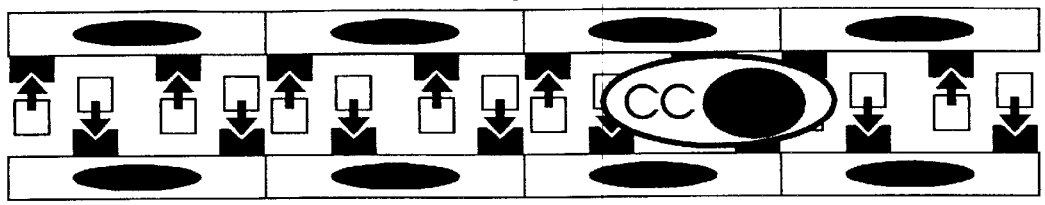
FIG. 9 is a schematic illustration of the site-directed chemotherapy according to the present invention as compared to the classical strategy of chemotherapy.
Figure 9A:
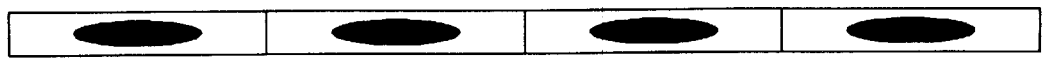
Figure 9A:
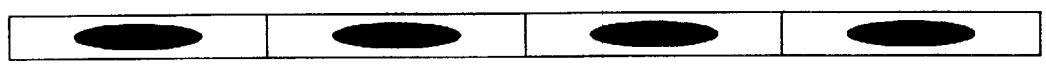
Figure 9B:
Figure 9B:
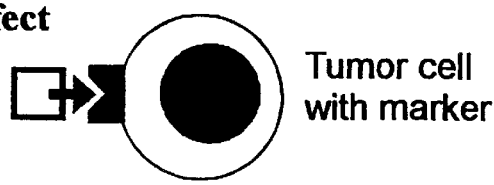
Figure 9B:
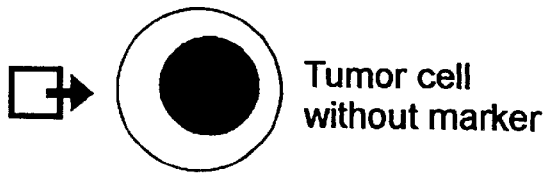

In an illustration of this embodiment and using standard methods known in the art and lipofectin as a transfection reagent, type 1 endothelial cells were transfected in culture with plasmid DNA carrying a gene encoding iNOS (NOS-2) under the control of the SV40 promoter. The transfected cells were selected for by growth in media containing neomycin. Transfected type 1 endothelial cells were then assayed for NO production. For comparison purposes, NO production was also assayed in transfected and activated type 1 endothelial cells treated with LNMA, activated type 2 endothelial cells, and activated type 2 endothelial cells treated with LNMA. As shown in FIG. 8, type 1 endothelial cells transfected with an expression vector producing iNOS under the control of the SV40 promoter (LEC-1 □) produces an amount of NO normalized to 100 μM; however, levels are typically at least one log greater as compared to that produced by activated type 2 endothelial cells (LEC-2 □). Note that the level of NO produced by type 2 endothelial cells has been shown to be sufficient to mediate tumoricidal activity. Likewise, treatment of each such cells with LNMA (LEC-1 ■; LEC-2 ■) results in a comparable inhibition of NO formation.

EXAMPLE 6

This example illustrates various embodiments of the mechanisms of delivery of the site-directed chemotherapy according to the present invention. As described above, and in U.S. Pat. No. 5,536,642, site-directed chemotherapy according to the present invention is directed to localizing targeted compositions to the prometastatic territories thereby directing therapy to metastatic colonies forming cells and/or to dormant metastatic tumor cells. Site-directed chemotherapy according to the present invention also encompasses, for primary non-lymphoid solid tumors having a high potential for metastasis (e.g., as predicted by IL-2Rα expression), "pre-treatment" of the prometastatic territories of the relevant organ in which metastases may develop as a preventative measure, e.g., to prevent the arrest and/or survival of any metastatic cells which may subsequently seed the organ. In this regard, it is known that primary tumors of certain organs have a predilection for metastasizing to certain areas. For example, breast tumors have a predilection for metastasizing to lymph nodes, lung, and bone; colon carcinomas have a predilection for metastasizing to lymph nodes, and the liver; rectal carcinomas have a predilection for metastasizing to the liver; melanomas have a predilection for metastasizing to lymph nodes, liver, brain and adrenal gland; ocular melanomas have a predilection for metastasizing to the liver; prostate carcinomas have a predilection for metastasizing to bone; and lung carcinomas have a predilection for metastasizing to the brain, and the liver.

As will be described in more detail, controlled delivery of the site-directed chemotherapy is achieved by infusing, such as by a catheter or functionally similar means, the chemotherapeutic agent into one or more vascular accesses that directly supplies the affected organ or site of the organ in which metastases may develop. The delivered chemotherapeutic agent then concentrates in the prometastatic territories of the organ by engaging its target via the targeting molecule portion of the chemotherapeutic agent. FIG. 9 summarizes the site-directed chemotherapy according to the present invention, and compares this method of treatment to the classical strategy of chemotherapy. Current treatment for malignancies (e.g., chemotherapy or radiation therapy) do not discriminate between normal and malignant cells, and hence, are associated with significant toxicity. By treating metastatic cells in the organ site in which they arrest and may subsequently develop into metastatic foci, the chemotherapeutic agent(s) is concentrated in the proximity of the metastatic cells, and the toxicity associated with systemic chemotherapy is ameliorated. The site-directed chemotherapy according to the present invention comprises providing one or more antitumor agents which are targeted to the sites at which metastatic cells arrest in organs in which metastases develop. The antitumor agents are targeted to either the arrested metastatic cells themselves via a cell-surface marker associated with metastasis; or are targeted type 1 endothelial cells comprising the predominate endothelial cell type in the prometastatic territory of the organ such that (a) any arrested metastatic tumor cells are then exposed to the chemotherapeutic agent, and/or (b) the endothelial cells are altered thereby inhibiting the ability of the metastatic tumor cells to arrest, survive, or proliferate in that site.

The basis principle underlying the site-directed chemotherapy according to the present invention involves introducing the chemotherapeutic agent into a vascular access (vein or artery) to the organ in which metastases have arrested, or will arrest. Infusion of cytotoxic drugs into arteries supplying an involved organ in a cancer patient has resulted in significant clinical benefit. For example, hepatic arterial infusion of fluoropyrimidines resulted in superior tumor response in patients as compared to the classical strategy of intravenous chemotherapy (*J. Natl. Cancer Inst.*, 1996, 88:252–8). The site-directed chemotherapy of the present invention has the added advantage in that, via the targeting molecule portion of the chemotherapeutic agent, the therapy is arrested in the prometastatic territories by binding a site selected from the group consisting of an arrested metastatic cell's surface molecule, or a cell-surface molecule present on type 1 endothelial cells (e.g., as illustrated in FIGS. 1 & 9). Also, the chemotherapeutic agent may further comprise a pharmaceutically acceptable carrier medium for facilitating infusion into the vascular access of the patient's organ to be treated.

In treating the liver with site-directed chemotherapy according to the present invention, a catheter may be inserted percutaneously into the main hepatic artery, or an accessory hepatic artery, branches thereof, or a vein supplying the liver, wherein the catheter is inserted via the femoral artery such as under image intensification (see, e.g., Shepherd et al., 1987, *J. Clin. Oncol.* 5:635–40; Takagi et al., 1983, *J. Surg. Oncol.* 23:219–22). The treatment may comprise multiple infusions of a pharmaceutically effective amount of the chemotherapeutic agent over time, as monitored by treatment response and by indicia of local toxicity in the treated organ. The catheter may be operatively connected to a portable pump such that the chemotherapeutic agent may be administered intermittently or continuously.

In treating the lung with site-directed chemotherapy according to the present invention, a catheter may be inserted into the pulmonary artery, or an accessory artery or branches thereof, or a vein supplying the lung, wherein the catheter is inserted using standard methods for inserting the catheter into such vasculature, as known to those skilled in the art. The treatment may comprise multiple infusions of a pharmaceutically effective amount of the chemotherapeutic agent over time, as monitored by treatment response and by indicia of local toxicity in the treated organ. The catheter may be operatively connected to a portable pump such that the chemotherapeutic agent may be administered intermittently or continuously.

In treating the brain with site-directed chemotherapy according to the present invention, a catheter may be inserted into the carotid artery, or an accessory artery or branches thereof, or a vein supplying the brain, wherein the catheter is inserted using standard methods for inserting the catheter into such vasculature, as known to those skilled in the art (see, e.g., Seiki et al., *Neurol. Med. Chir.* 1991, 31:695–701; Bouvier et al., 1987, *Neurosurgery* 20:286–91). The treatment may comprise multiple infusions of a pharmaceutically effective amount of the chemotherapeutic agent over time, as monitored by treatment response and by indicia of local toxicity in the treated organ. The catheter may be operatively connected to a portable pump such that the chemotherapeutic agent may be administered intermittently or continuously.

In treating lymph nodes with site-directed chemotherapy according to the present invention, a catheter may be inserted into one or more of the major nodal arteries that supply the lymph nodes, or an accessory artery or branches thereof, or a vein that supplies the lymph nodes, wherein the catheter is inserted using standard methods for inserting the catheter into such vasculature, as known to those skilled in the art. The treatment may comprise multiple infusions of a pharmaceutically effective amount of the chemotherapeutic agent over time, as monitored by treatment response and by indicia of local toxicity in the treated organ. The catheter may be operatively connected to a portable pump such that the chemotherapeutic agent may be administered intermittently or continuously.

In treating an adrenal gland with site-directed chemotherapy according to the present invention, a catheter may be inserted into one or more of the major arteries that supply the adrenal gland, or an accessory artery or branches thereof, or a vein that supplies the adrenal gland, wherein the catheter is inserted using standard methods for inserting the catheter into such vasculature, as known to those skilled in the art. The treatment may comprise multiple infusions of a pharmaceutically effective amount of the chemotherapeutic agent over time, as monitored by treatment response and by indicia of local toxicity in the treated organ. The catheter may be operatively connected to a portable pump such that the chemotherapeutic agent may be administered intermittently or continuously.

In treating bone marrow with site-directed chemotherapy according to the present invention, a catheter may be inserted into one or more of the major arterial vessels of the periosteal arteriole system that supply the bone marrow, or into a vein that supplied the bone, or into the bone marrow itself, using standard methods for inserting the catheter into such vasculature, as known to those skilled in the art. The treatment may comprise multiple infusions of a pharmaceutically effective amount of the chemotherapeutic agent over time, as monitored by treatment response and by indicia of local toxicity in the treated organ. The catheter may be operatively connected to a portable pump such that the chemotherapeutic agent may be administered intermittently or continuously.

EXAMPLE 7

This example illustrates various embodiments of the targeting molecule portion of the chemotherapeutic agent according to the present invention which is used in the site-directed chemotherapy. As described above, and in U.S. Pat. No. 5,536,642, the targeting molecule is at least one composition selected from the group consisting of a lectin having binding specificity for N-acetyl neuraminic acid (NANA) and/or N-acetyl galactosamine (GalNAC), a monoclonal antibody or fragment thereof having binding specificity for an endothelial cell adhesion molecule that is preferentially expressed in type 1 endothelial cells as compared to other subpopulations of endothelial cells contained in the sinusoidal area of an organ in which metastases develop (e.g., ICAM-1), a monoclonal antibody or fragment thereof having binding specificity for IL-2Rα, and a composition comprising IL-2.

A lectin having binding specificity for NANA or GalNAC or both NANA and GalNAC, may be selected from the group consisting of Dolichos biflorus agglutinin (DBA), soybean agglutinin (SPA), Maclura pomifera agglutinin (MPA), Phaeolepiota aurea lectins 1 and 2 (PAL-I, PAL-II), Moluccella laevis lectin (MLL), peanut agglutinin (PNA), Vicia villosa agglutinin (WA), Sophora japonica agglutinin (SJA), Caragana arborescens agglutinin (CAA), Griffonia simplicifolia lectin (BSI-A4), Bauhinia purpurea agglutinin (BPA), and Helix aspersa agglutinin (HAA); lectins binding NANA such as Limax flavus lectin (LFA), and limulin; and lectins binding both GalNAC and NANA including wheat germ agglutinin (WGA). An illustration of the specificity of such a lectin for targeting type 1 endothelial cells comprising the prometastatic territory is illustrated in FIG. 1.

Additionally, as disclosed herein, the targeting molecule may at least one composition selected from the group consisting of a compound or composition comprising mannose, a compound or composition comprising glycated albumin, and a ligand that binds to ICAM-1. As shown in Table 2 herein, certain cell surface molecules preferentially expressed on unactivated (and activated) type 1 endothelial cells may be used as a target to which the targeting portion of the chemotherapeutic agent may be directed. These cell-surface molecules include mannose receptor, polypeptides having binding affinity for glycated albumin (GA), and ICAM-1. Thus, ligands having binding specificity for mannose receptor or for ICAM-1 may be used as the targeting molecule. Additionally, glycated albumin may be used as the targeting molecule.

In regards to activated type 1 endothelial cells, it is noted that TNFα and IFNγ may further induce expression of ICAM-1, as these cytokines have been reported to induce ICAM-1 expression in other cell types (Buckle et al., 1990, *Eur. J. Inmmunol.* 20:337–41; Pohlman et al., 1986, *J. Inumunol.* 136:4548–53). Also, impairment of endothelial function, specifically inhibition of NO synthase, has been shown to induce tissue hypoxia. Hypoxia has also been shown to upregulate the expression of ICAM-1 by endothelium (Setty and Stuart, 1996, *Blood* 88:2311–20). Thus, a ligand having binding specificity for ICAM-1 may be used as the targeting molecule. In addition to an anti-ICAM-1 monoclonal antibody (including fragment thereof), a ligand having binding specificity for ICAM-1 may be selected from the group consisting of a beta 2-integrin, LFA-1, and Mac-1 (see, e.g., Lawrence et al., 1995, *Eur. J. Immunol.* 25:1025–31).

In regards to activated type 1 endothelial cells, it is noted that a cytokine which activates type 1 endothelial cells (IL-1β) can upregulate expression of mannose receptor (Asumendi et al., 1996, *Hepatology* 23:1521–9). Thus, a ligand having binding specificity for mannose receptor may be used as the targeting molecule. A ligand having binding specificity for mannose receptor may be selected from the group consisting of mannan, mannose, mannosylated-proteins (e.g., serum albumin, tissue-type plasminogen activator, beta-glucuronidase), and an anti-mannose receptor monoclonal antibody (including fragment thereof).

There are several methods known in the art for conjugating a antitumor agent to a targeting molecule. Depending on the nature of the targeting molecule, such methods may include, but are not limited to, the use of glutaraldehyde, or succinimidyl m-maleimidobenzoate, or 1-ethyl-3-(3-dimethylaminopropyl) carbodiimide, or by using bromoacetylated targeting molecule, direct conjugation to a protein targeting molecule by cyanogen bromide, reductive amination, or by using bifunctional linkers. Such bifunctional linkers include, but are not limited to, N-hydroxy succinimide-based linkers cystamine, glutaraldehyde, and diamino hexane.

EXAMPLE 8

This example illustrates various embodiments of the antitumor agent portion of the chemotherapeutic agent according to the present invention which is used in the site-directed chemotherapy. Further, an embodiment illustrating use of the chemotherapeutic agent in the site-directed method according to the present invention is disclosed. As described above, and in U.S. Pat. No. 5,536,642, the antitumor agent is a therapeutically effective amount of at least one composition selected from the group consisting of a toxin, radionuclide, and antineoplastic drug. Additionally, as disclosed herein, the antitumor agent may be a therapeutically effective amount of at least one composition selected from the group consisting of an inhibitor of IL-1β, an antagonist of IL-1β, an inhibitor of GM-CSF, an antagonist of GM-CSF, an inhibitor of IL-6, an antagonist of IL-6, an inhibitor of IL-10, an antagonist of IL-10, an inhibitor of TNF-α, an antagonist of TNF-α, an inhibitor of IFNγ, an antagonist of IFNγ, and an inducer of NO production.

In one illustration of the site-directed chemotherapy according to the present invention, targeted are metastatic cells which are arrested in the prometastatic territories, and are in a dormant state or slow proliferative state (pseudo-resting) that is highly resistant to NK cells and to certain antitumor agents. Such metastatic cells come out of each of these states under the influence of low local concentrations of IL-2 and IL-1. Even though IL-2Rα has a low affinity for IL-2, a relatively small dose of IL-2 concentrated in the prometastatic territories will activate resting metastatic tumor cells which makes them more susceptible to antineoplastic drugs. Thus according to this illustration of the method according to the present invention, and using a mechanism of delivery such as illustrated in Example 6 herein, a method for treating metastatic cells in a slow proliferative state or dormant state comprises simultaneous delivery of IL-2 (or IL-1) and a chemotherapeutic agent to the prometastatic territories, wherein the chemotherapeutic agent comprises a targeting molecule according to the present invention linked to an antitumor agent that is active against rapidly dividing cells (e.g., antineoplastic drug). When the proliferation of blastic metastatic cells are triggered by IL-2 (or IL-1), they become more sensitive to such antineoplastic drugs and to NK cells.

Figure 10A:
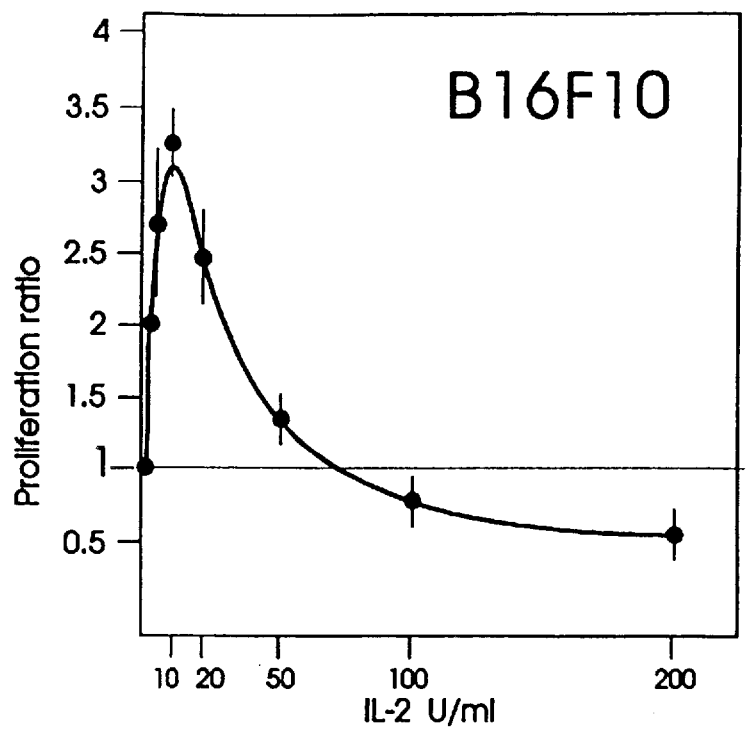
FIG. 10A is a graph illustrating B16F10 cell proliferation relative to IL-2 concentration.
Figure 10B:
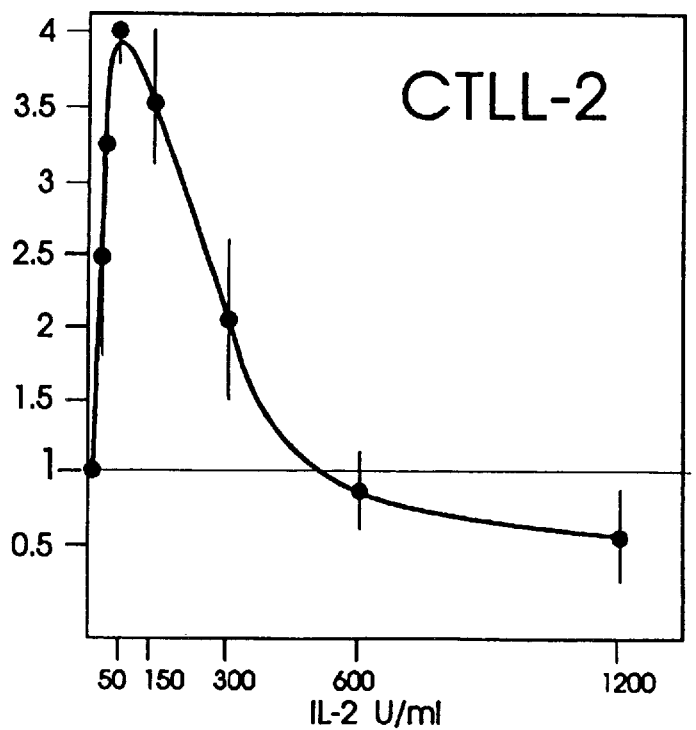
FIG. 10B is a graph illustrating CTLL-2 cell proliferation relative to IL-2 concentration.

As an illustration of the correlation of cytokine concentration and the resultant effects on non-lymphoid tumor cells growth, B16F10 melanoma cells were exposed to different concentrations of IL-1 and IL-2, and the resulting growth response was noted. For the measurement of IL-2 effect on B16F10 melanoma cell growth, $10^4$ viable cancer cells were added to each well of a 96 well plate and the cultures were incubated at 5%$CO_2$ for 48 hours in serum-free or 10% fetal bovine serum supplemented regular media containing a concentration of mouse recombinant IL-2 ranging from 10–200 U/ml; or 20, 125, or 250 U human recombinant IL-2 (hrIL-2). Then each well was pulsed with 1 $\mu$Ci of [$^3$H]-thymidine, and harvested after 6 hours wherein the radio-activity was subsequently measured. In a protocol for the measurement of IL-1 effect on B16F10 melanoma cell growth, $10^4$ viable cancer cells were added to each well of a 96 well plate and the cultures were incubated at 5%$CO_2$ for 48 hours in serum-free or 10% FBS supplemented regular media containing either 1, 10 or 20 U/ml mouse IL-1β. In some cases, anti IL-2Rα antibody was added simultaneously with the IL-1β. Each well was pulsed with 1 $\mu$Ci of [$^3$H]-thymidine, and harvested after 6 hours wherein the radio-activity was subsequently measured. FIG. 10A shows that high concentrations (greater than 75 U/ml) of IL-2 induces death or blastic cell cytostasis but does not affect the B16F10 metastatic cells in pseudo-resting state. Of therapeutic importance, note that IL-2 concentrations greater than 75 U/ml have a suppressing effect on cell growth of metastatic cells, and that concentrations of between 75 U/ml and 100 U/ml are not toxic for lymphocytes (FIG. 10B, represented by CTLL-2) prepared in a similar manner. Table 4 shows that IL-2 or IL-1, in low concentrations, induces the step from pseudo-resting to blastic and induces the blastic cells proliferation.

TABLE 4

| Cytokine/concentration | B1GF10 Response (mean, cpm) |
| --- | --- |
| Control | 60.12 ± 28.5 |
| anti-IL-2Rα antibody | 40.60 ± 7.9 |
| Mouse IL-2 (10 U/ml) | 2057.40 ± 540.7 |
| Mouse IL-2 (20 U/ml) | 3619.60 ± 116.2 |
| IL-1 (1 U/ml) | 61.85 ± 20.5 |
| IL-1 (10 U/ml) | 1083.30 ± 70.5 |
| IL-1 (20 U/ml) | 2045.60 ± 448.2 |
| IL-1 (10 U/ml) + | 571.19 ± 78.2 |

TABLE 4-continued

| Cytokine/concentration | B1GF10 Response (mean, cpm) |
| --- | --- |
| anti-IL-2Rα antibody (1 μg/ml) IL-1 (10 U/ml) + anti-IL-2Rα antibody (4 μg/ml) | 98.64 ± 16.8 |
| FCS (10%) Control | 1594.30 ± 301.3 |
| anti-IL-2Rα antibody (4 μg/ml) | 565.40 ± 66.9 |
| Mouse IL-2 (20 U/ml) | 2556.60 ± 566.2 |
| FCS (10%) Control | 2135.32 ± 245.5 |
| hrIL-2 (20 U/ml) | 2012.52 ± 347.2 |
| hrIL-2 (125 U/ml) | 2452.22 ± 298.3 |
| hrIL-2 (250 U/ml) | 3181.62 ± 231.6 |

Thus, low doses of IL-2 (e.g., <100 U/ml) induce growth of metastatic cells; whereas high doses (e.g., >500 U/ml) induce apoptosis of metastatic cells.

Additionally, the IL-1 or IL-2 may be linked to a targeting molecule according to the present invention, so that the IL-1 or IL-2 (like the chemotherapeutic agent) is delivered to the prometastatic territories (either to the metastatic cells or to type 1 endothelial cells), thereby coming in contact with the metastatic cells. For example, an anti-ICAM antibody may be linked to the IL-1 or IL-2, and the same antibody linked to the antitumor agent, and those components are then mixed in a therapeutically effective ratio to provide a composition with higher affinity to the prometastatic territories. Additionally, either IL-1 or IL-2 and/or the antitumor agent may be incorporated into carrier liposomes, using methods known to those skilled in the art, to increase retention time of the compound at the prometastatic territories. Such liposomes contain the targeting molecule extending from the liposomes so as to bind to its specific target. To investigate this embodiment, liposomes have been constructed which contain rhodamine inside and with incorporated WGA at the surface. Injection of these liposomes into the portal vein of the liver resulted in the same distribution of fluorescence as depicted in FIG. 1. In addition it was noted that the type 1 endothelial cells did not internalize the lectin-liposomes, leaving them exposed to the adjacent metastatic cells. However, a possible limitation is that it appears by the fluorescence analysis, that Kupffer cells phagocytosed a small portion of the lectin-liposome composition. Additionally, it will be appreciated by one skilled in the art that a pharmaceutically acceptable carrier medium, other than liposomes, may be used for facilitating infusion of the chemotherapeutic agent into the vascular access of the patient's organ to be treated.

Illustrated in this embodiment of a method according to the present invention is site-directed chemotherapy targeted to metastatic cells in a slow proliferative state or dormant state in the prometastatic territories. The advantages of such a method include directly targeting the antitumor agent to cells in the prometastatic territories in the specific organ, thereby achieving therapeutic concentrations of the antitumor agent in the area where metastases of solid non-lymphoid tumor cells are localized, with minimal harm to the immune and the hematopoietic systems.

EXAMPLE 9

This example illustrates another embodiment in which a chemotherapeutic agent is used in the site-directed method according to the present invention. In the following embodiment used to illustrate the invention, it is important to note that mice have been validated as a model for the evaluation of chemotherapeutic agents because the model has been shown to reflect the clinical effectiveness of chemotherapeutic agents in original patients treated with these agents; and reflects antitumor effects from the agents, such as tumor regression or inhibition of tumor growth, as consistent with the activity against the corresponding types of clinical cancer (See for example, Neuwalt et al., 1985, Cancer Res. 45:2827–2833; Ovejera et al., 1978, Annals of Clin. and Lab. Science 8:50).

A chemotherapeutic agent comprised the lectin wheat germ agglutinin conjugated to the antitumor agent 5-fluorouracil (5-FU). The conjugate was made by mixing poly-1-lysine (14 mg) with a photoactivatable cross-linker (60 mg; N-succinimidyl-6-[4'-azido-2'-nitrophenylamino] hexanate) in 0.1 M bicarbonate buffer, pH 8.5, in the dark. The reaction was left at room temperature for 1 hour in the dark. Free cross-linker was separated from cross-linker bound to lysine using dialysis with bicarbonate buffer and by optical density. Next, 5-FU (45 mg) was added to the cross-linker-lysine mixture, and exposed to light (30 flashes) by using the standard flash from a 35 mm camera. The resultant composition, 5-FU-cross-linker-lysine, was extensively dialyzed versus bicarbonate buffer to remove any unbound 5-FU. Lectin (2 mg) was added to the composition in the presence of dimethyl adipimidate-2-HCl (DMA), and incubated for 30 minutes at room temperature. The resultant composition was extensively dialyzed versus bicarbonate buffer to remove free WGA and DMA. The final product was the chemotherapeutic agent comprising WGA-poly-1-lysine-cross-linker-5-fluorouracil.

Figure 11A:
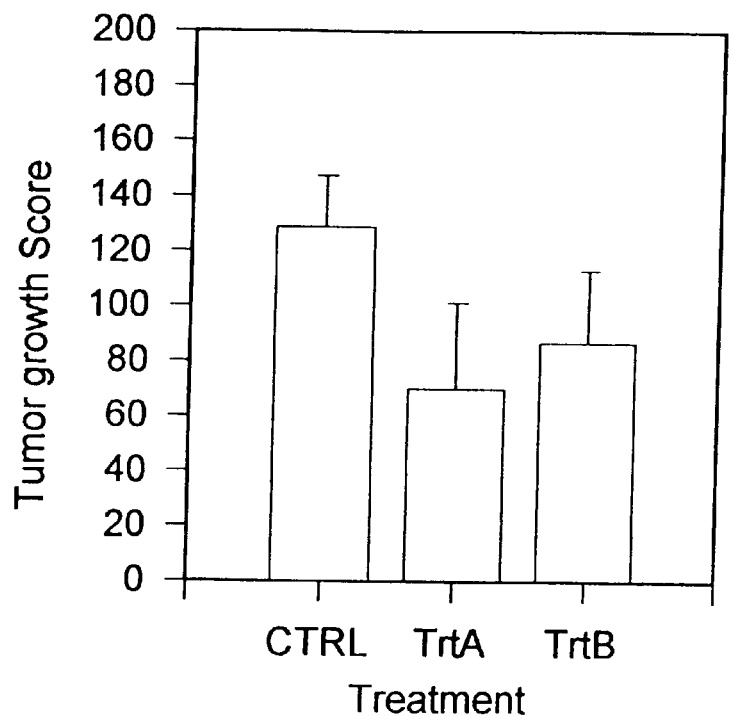
FIG. 11A is a bar graph showing the effect of various anticancer therapies, as compared to a control, on spleen tumor size and abdominal metastases.
Figure 11B:
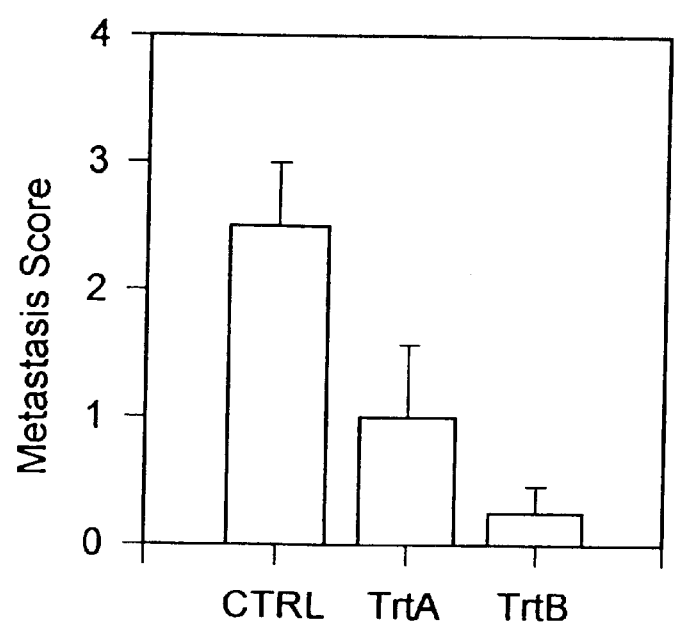
FIG. 11B is a bar graph showing the effect of various anticancer therapies, as compared to a control, on liver metastases.

The experimental model used to evaluate treatment targeted to the prometastatic territories of the liver and spleen involved three groups of SCID mice which had been challenged with melanoma tumor cells by intrasplenic injection. Each of the mice received a challenge of $5 \times 10^5$ melanoma cells. One group of 10 tumor-bearing mice were the control group which received 200 μl of phosphate buffered saline (PBS) into the tail vein on days 2, 4, 6, 8, 10, 12, and 14. A second group of 10 tumor-bearing mice received 5 μg of 5-FU (in 200 μl of PBS; "treatment A") into the tail vein on days 2, 4, 6, 8, 10, 12, and 14. A third group of 10 tumor-bearing mice received 5 μg of the chemotherapeutic agent (5-FU-conjugated WGA in 200 μl of PBS; "treatment B") into the tail vein on days 2, 4, 6, 8, 10, 12, and 14. Tumor load was analyzed on day 15 by evaluating spleen tumor size and abdominal lymph node metastasis (scored together), and liver metastasis (scored by evaluating size and number of metastases). The results showing treatment with no chemotherapeutic agent or drug ("CTRL"), with 5-FU treatment alone ("TrtA"), and treatment with the targeted chemotherapeutic agent ("TrtB") are illustrated in FIG. 11A (spleen tumor and abdominal metastasis) and FIG. 11B (liver metastasis). As shown in FIGS. 11A and 11B, treatment with the chemotherapeutic agent reduced spleen tumor size and abdominal lymph node metastases, and significantly reduced occurrence of liver metastasis.

In a similar experiment, a group of tumor bearing mice were treated with the chemotherapeutic agent (5-FU conjugated to WGA) using the therapeutic regimen as described above. The mice were followed over time. At day 40, some mice were evaluated for metastases, wherein the livers showed no sign of metastases. The mice were followed over 120 days, without signs of metastasis and with no significant decrease in lymphocytes or hematopoietic cells.

In summary, the method of site-directed chemotherapy according to the present invention, a patient having metastases in an organ, or suspected of developing metastases in that organ, is treated with a therapeutically effective amount of a chemotherapeutic agent according to the present invention. The targeting molecule portion of the chemotherapeutic agent directs and arrests the antitumor agent portion to the prometastatic territories of the organ by targeting the antitumor agent to either the arrested metastatic cells themselves via a cell-surface marker associated with metastasis; or are targeted to the type 1 endothelial cells comprising the prometastatic territories such that (a) any arrested metastatic tumor cells are then exposed to the antitumor agent, and/or (b) the endothelial cells are altered thereby inhibiting the ability of the metastatic tumor cells to arrest, survive, or proliferate in that site.

From the foregoing, it will be obvious to those skilled in the art that various modifications in the above-described methods, and compositions can be made without departing from the spirit and scope of the invention. Accordingly, the invention may be embodied in other specific forms without departing from the spirit or essential characteristics thereof. Present embodiments and examples, therefore, are to be considered in all respects as illustrative and not restrictive, and all changes which come within the meaning and range of equivalency of the claims are therefore intended to be embraced therein.

What is claimed is:

1. A method of site-directed chemotherapy of metastatic cells of non-lymphoid tumor origin, wherein the metastatic cells are in a state selected from the group consisting of a dormant state, and a pseudo-resting state, said site-directed chemotherapy is directed to prometastatic territories of a target organ having or suspected of having arrested metastatic cells, and said method comprises concentrating in the prometastatic territories by introducing directly into a vascular access of the organ:

(a) a therapeutically effective amount of a component selected from the group consisting of IL-2, and IL-1, to activate pseudo-resting or dormant metastatic cells; and (b) a chemotherapeutic agent comprised of a targeting molecule linked to an antitumor agent, wherein the targeting molecule has binding specificity for a cell-surface molecule preferentially expressed by type 1 endothelial cells as compared to expression by type 2 endothelial cells in the prometastatic territories, and wherein the antitumor agent is a therapeutically effective amount of an agent active against proliferating cells which contacts and effects death of proliferating metastatic cells if present in the prometastatic territories.

2. The method according to claim 1, further comprising linking the IL-2 or IL-1 to a targeting molecule having binding specificity for a cell-surface molecule preferentially expressed by type 1 endothelial cells, wherein the cell-surface molecule is selected from the group consisting of N-acetyl neuraminic acid, N-acetyl galactosamine, ICAM-1, mannose receptor, and a membrane-associated polypeptide that binds glycated albumin.

3. The method according to claim 2, wherein the targeting molecule is selected from the group consisting of a lectin having binding specificity for N-acetyl neuraminic acid, a lectin having binding specificity for N-acetyl galactosamine, a monoclonal antibody or fragment thereof having binding specificity for ICAM-1, a compound or composition comprising mannose, a compound or composition comprising glycated albumin, and a ligand that binds to ICAM-1.

4. The method according to claim 1, wherein the component and the chemotherapeutic agent further comprises a pharmaceutically acceptable carrier medium to facilitate infusion into the vascular access of the organ.

5. A method of site-directed chemotherapy of metastatic cells of non-lymphoid tumor origin, said site-directed chemotherapy is directed to prometastatic territories of a target organ, said method comprises concentrating in the prometastatic territories by introducing directly into a vascular access of the organ having, or suspected of having, arrested metastatic cells, a therapeutically effective amount of a chemotherapeutic agent; wherein the chemotherapeutic agent is targeted to type 1 endothelial cells in a process selected from the group consisting of exposing any arrested metastatic cells present in the prometastatic territories to the chemotherapeutic agent, altering the type 1 endothelial cells thereby inhibiting the ability of metastatic cells to arrest or survive or proliferate in that site, and a combination thereof; and wherein the chemotherapeutic agent is comprised of a targeting molecule linked to an antitumor agent, wherein the targeting molecule has binding specificity for a cell-surface molecule preferentially expressed by type 1 endothelial cells as compared to expression by type 2 endothelial cells in the prometastatic territories.

6. The method according to claim 5, wherein the chemotherapeutic agent is targeted to type 1 endothelial cells by a targeting molecule selected from the group consisting of a lectin having binding specificity for N-acetyl neuraminic acid, a lectin having binding specificity N-acetyl galactosamine, a monoclonal antibody or fragment thereof having binding specificity for ICAM-1, a compound or composition comprising mannose, a compound or composition comprising glycated albumin, and ligand that binds to ICAM-1.

7. The method according to claim 5, wherein the chemotherapeutic agent is targeted to type 1 endothelial cells in a process of altering the type 1 endothelial cells so as to inhibit the ability of metastatic cells to arrest or survive or proliferate in the treated site, and wherein the antitumor agent is in a therapeutically effective amount and selected from the group consisting of an inhibitor of IL-1$\beta$, an antagonist of IL-1$\beta$, an inhibitor of GM-CSF, an antagonist of GM-CSF, an inhibitor of IL-6, an antagonist of IL-6, an inhibitor of IL-10, an antagonist of IL-10, an inhibitor of TNF-$\alpha$, an antagonist of TNF-$\alpha$, an inhibitor of IFN$\gamma$, an antagonist of IFN$\gamma$, and an inducer of NO production.

8. The method according to claim 5, wherein the chemotherapeutic agent further comprises a pharmaceutically acceptable carrier medium to facilitate infusion into the vascular access of the organ.

9. A method for delivering and concentrating a therapeutically effective amount of a chemotherapeutic agent to type 1 endothelial cells contained in prometastatic territories of an organ, the method comprises introducing the chemotherapeutic agent directly into a vascular access of the organ, wherein the chemotherapeutic agent is comprised of a targeting molecule linked to an antitumor agent, and wherein the targeting molecule has binding specificity for a cell-surface molecule preferentially expressed by type 1 endothelial cells as compared to expression by type 2 endothelial cells in the prometastatic territories.

10. The method according to claim 9, wherein the chemotherapeutic agent is targeted to type 1 endothelial cells in a process of altering the type 1 endothelial cells so as to inhibit the ability of metastatic cells to arrest or survive or proliferate in the treated site, and wherein the antitumor agent is in a therapeutically effective amount and selected from the group consisting of an inhibitor of IL-1$\beta$, an antagonist of IL-1$\beta$, an inhibitor of GM-CSF, an antagonist of GM-CSF, an inhibitor of IL-6, an antagonist of IL-6, an inhibitor of IL-10, an antagonist of IL-10, an inhibitor of TNF-$\alpha$, an antagonist of TNF-$\alpha$, an inhibitor of IFN$\gamma$, an antagonist of IFN$\gamma$, and an inducer of NO production.

11. The method according to claim 9, wherein the chemotherapeutic agent further comprises a pharmaceutically acceptable carrier medium to facilitate infusion into the vascular access of the organ.

12. A chemotherapeutic agent for use in effecting cell death of metastatic tumor cells of solid nonlymphoid tumor origin that may be arrested in a target organ, wherein the chemotherapeutic agent is comprised of a targeting molecule linked to a therapeutically effective amount of an antitumor agent, wherein the targeting molecule has binding specificity for a cell-surface molecule preferentially expressed by type 1 endothelial cells as compared to expression by type 2 endothelial cells in prometastatic territories of the target organ, and wherein the antitumor agent is in a therapeutically effective amount and selected from the group consisting of an inhibitor of IL-1β, an antagonist of IL-10, an inhibitor of GM-CSF, an antagonist of GM-CSF, an inhibitor of IL-6, an antagonist of IL-6, an inhibitor of IL-10, an antagonist of IL-10, an inhibitor of TNF-α, an antagonist of TNF-α, an inhibitor of IFNγ, an antagonist of IFNγ, and an inducer of NO production.

* * * * *